(12) United States Patent
Ghahary et al.

(10) Patent No.: US 10,865,811 B2
(45) Date of Patent: Dec. 15, 2020

(54) ENGINEERED TISSUE SUBSTITUTE SYSTEM

(71) Applicant: THE UNIVERSITY OF BRITISH COLUMBIA, Vancouver (CA)

(72) Inventors: Aziz Ghahary, Vancouver (CA); Ryan Hartwell, Vancouver (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 15/547,320

(22) PCT Filed: Feb. 3, 2016

(86) PCT No.: PCT/CA2016/000032
§ 371 (c)(1),
(2) Date: Jul. 28, 2017

(87) PCT Pub. No.: WO2016/123693
PCT Pub. Date: Aug. 11, 2016

(65) Prior Publication Data
US 2018/0031005 A1 Feb. 1, 2018
US 2018/0258960 A9 Sep. 13, 2018
US 2019/0010963 A9 Jan. 10, 2019

Related U.S. Application Data

(60) Provisional application No. 62/112,883, filed on Feb. 6, 2015.

(51) Int. Cl.
| | |
|---|---|
| *F15B 1/16* | (2006.01) |
| *C12N 5/00* | (2006.01) |
| *A61L 27/60* | (2006.01) |
| *A61L 27/26* | (2006.01) |
| *A61L 27/52* | (2006.01) |
| *A61L 27/48* | (2006.01) |
| *E21B 33/064* | (2006.01) |
| *F15B 1/24* | (2006.01) |

(52) U.S. Cl.
CPC .............. *F15B 1/165* (2013.01); *A61L 27/26* (2013.01); *A61L 27/48* (2013.01); *A61L 27/52* (2013.01); *A61L 27/60* (2013.01); *C12N 5/0068* (2013.01); *E21B 33/064* (2013.01); *F15B 1/24* (2013.01); *A61L 2300/64* (2013.01); *A61L 2400/06* (2013.01); *C12N 2533/54* (2013.01); *C12N 2533/70* (2013.01); *C12N 2537/10* (2013.01); *F15B 2201/205* (2013.01); *F15B 2201/31* (2013.01); *F15B 2201/32* (2013.01); *F15B 2201/41* (2013.01)

(58) Field of Classification Search
CPC ........ F15B 1/165; F15B 1/24; F15B 2201/32; F15B 2201/3152; F15B 2201/31; F15B 2201/205; F15B 2201/41; E21B 33/064; A61L 27/52; A61L 27/48; A61L 27/26; A61L 27/60; A61L 2300/64; A61L 2400/06; C12N 5/0068; C12N 2537/10; C12N 2533/70; C12N 2533/54; A61P 17/02

See application file for complete search history.

(56) References Cited

U.S. PATENT DOCUMENTS

2005/0271727 A1  12/2005  Yao

FOREIGN PATENT DOCUMENTS

| JP | 2010537711 A | 12/2010 |
|---|---|---|
| JP | 2014532713 A | 12/2014 |
| WO | 2009028965 A1 | 3/2009 |
| WO | 2009/042514 A1 | 4/2009 |
| WO | 2013067195 A1 | 5/2013 |

OTHER PUBLICATIONS

Hartwell, R., et al., "An In-Situ Forming Skin Substitute Improves Healing Outcome in a Hypertrophic Scar Model," Tissue Engineering Part A 21(5-6):1085-1094, Mar. 2015.
Hartwell, R. et al., "A Novel Hydrogel-Collagen Composite Improves Functionality of an Injectable Extracellular Matrix," Acta Biomaterialia 7(8): 3060-3069, Aug. 2011.
Zhang, L., et al., "Preparation of Collagen-Chondroitin Sulfate-Hyaluronic Acid Hybrid Hydrogel Scaffolds and Cell Compatibility in Vitro," Carbohydrate Polymers 84(1):118-125, Feb. 2011.
International Search Report and Written Opinion dated Apr. 27, 2016, issued in International Application No. PCT/CA2016/000032, filed Feb. 3, 2006, 13 pages.
International Preliminary Report on Patentability dated Aug. 8, 2017, issued in International Application No. PCT/CA2016/000032, filed Feb. 3, 2006, 9 pages.
Hartwell, R., et al., "Polyvinyl Alcohol-Graft-Polyethylene Glycol Hydrogels Improve Utility and Biofunctionality of Injectable Collagen Biomaterials," Biomedical Materials 11(8):35013, Jun. 2016.
Hosseini-Tabatabaei, A., et al., "Embedding Islet in a Liquid Scaffold Increases Islet Viability and Function," Canadian Journal of Diabetes 37(1):27-35, Feb. 2013.
Kamoun, E., et al., "Crosslinked Poly(Vinyl Alcohol) Hydrogels for Wound Dressing Applications: A Review of Remarkably Blended Polymers," Arabian Journal of Chemistry 8(1):1-14, Jan. 2015.
Extended European Search Report dated May 15, 2018, issued in European Application No. 16746019.5, filed Feb. 3, 2016, 9 pages.
INTEGRA Flowable Wound Matrix 510(k) Summary, dated Oct. 10, 2007, 4 pages.

(Continued)

*Primary Examiner* — Snigdha Maewall
(74) *Attorney, Agent, or Firm* — Christensen O'Connor Johnson Kindness PLLC

(57) ABSTRACT

Compositions and methods of preparation and use are provided for an engineered tissue substitute system comprising collagen, glycosaminoglycan and hydrogel in a cross-linked matrix. The compositions may be further lyophilized and reconstituted with a physiological fluid prior to use in methods, such as in the treatment of wounds, tissue engineering and cell transplantation.

25 Claims, 10 Drawing Sheets

(56) References Cited

OTHER PUBLICATIONS

Sano, M., et al., "Structure and Properties of Borate Crosslinked Poly(Vinyl Alcohol) Gel Films," Journal of Textile Society 48(2):74-83, 1992.
Notice of Reasons for Refusal dated Dec. 29, 2019, issued in JP Application No. 2017541349, filed Feb. 3, 2016, 10 pages.

FIGURE 1

| TYPE I Collagen is combined with Collagen buffer and NaOH on ice at pH 7.0. |

| Glycosaminoglycan (GAG), Chondroitin-6-sulfate, is mixed into the Collagen. |

| Glutaraldehyde is then combined with dextran (in the dark) and mixed into the Collagen-Glycosaminoglycan mixture. |

| Following incubation, polyvinyl alcohol (PVA)-co-polyethylene glycol (PEG), is combined with the Collagen-Glycosaminoglycan mixture, followed by sodium-tetraborohydrate and ascorbic acid. |

| The Collagen-Glycosaminoglycan-PVA-PEG mixture is lyophilized (frozen at -80°C and freeze-dried). |

| The lyophilized Collagen-Glycosaminoglycan-PVA-PEG is powdered (may be stored up to 1 month at 21°C). |

| The powdered lyophilized Collagen-Glycosaminoglycan-PVA-PEG is reconstituted with an aqueous solvent (for example, water, media, blood, plasma, or serum). |

| The reconstituted powdered lyophilized Collagen-Glycosaminoglycan-PVA-PEG may be casted within 15-20 minutes of the addition if aqueous solvent at 34-37°C. |

FIGURE 2
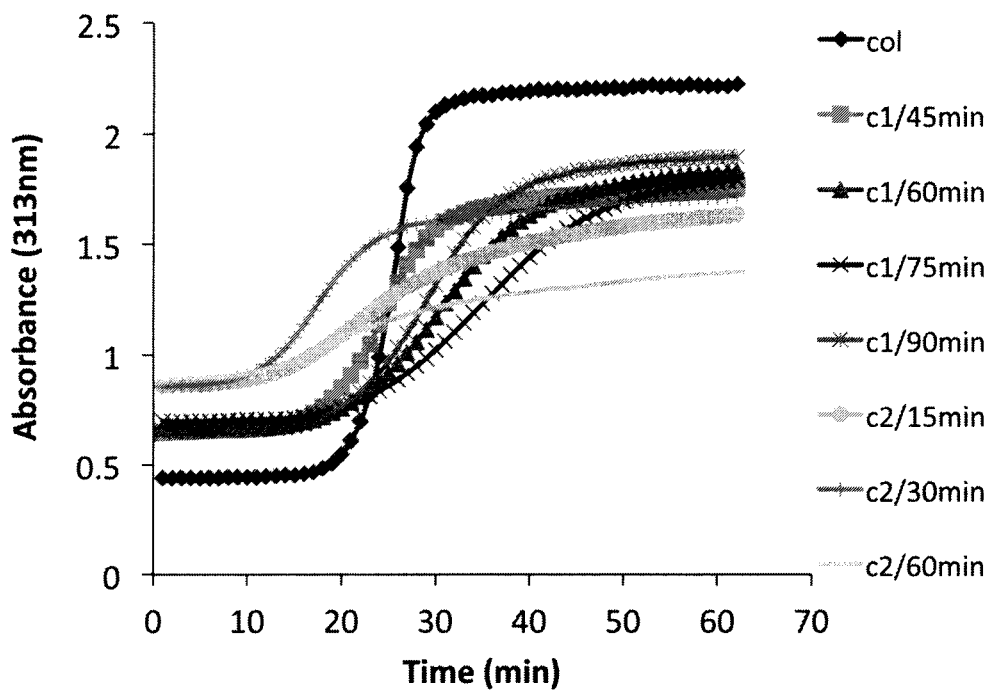
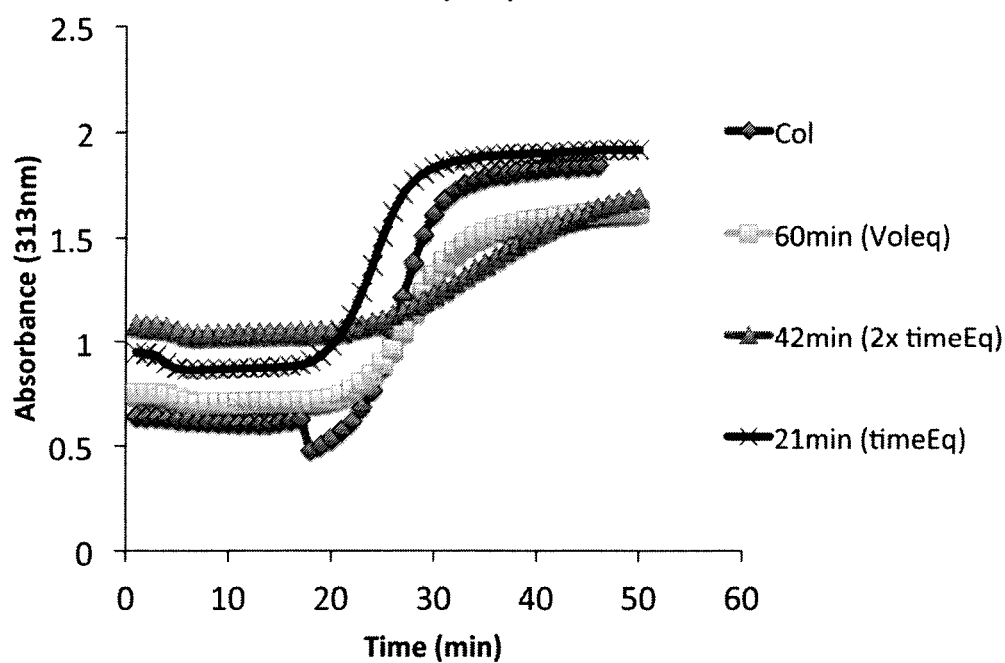

FIGURE 4
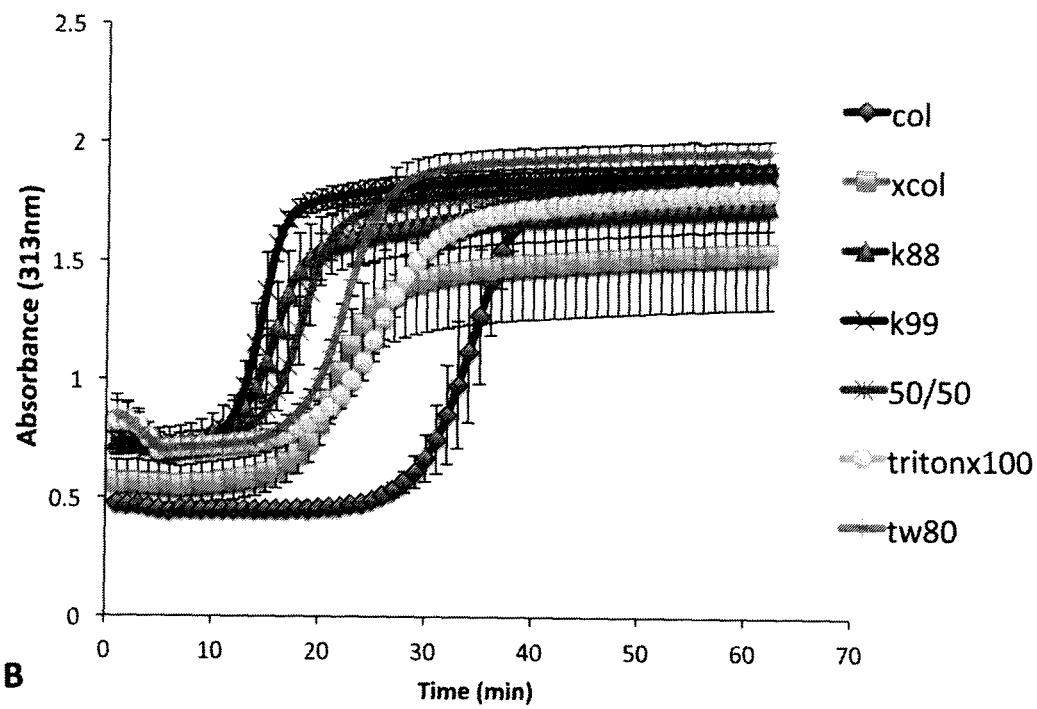
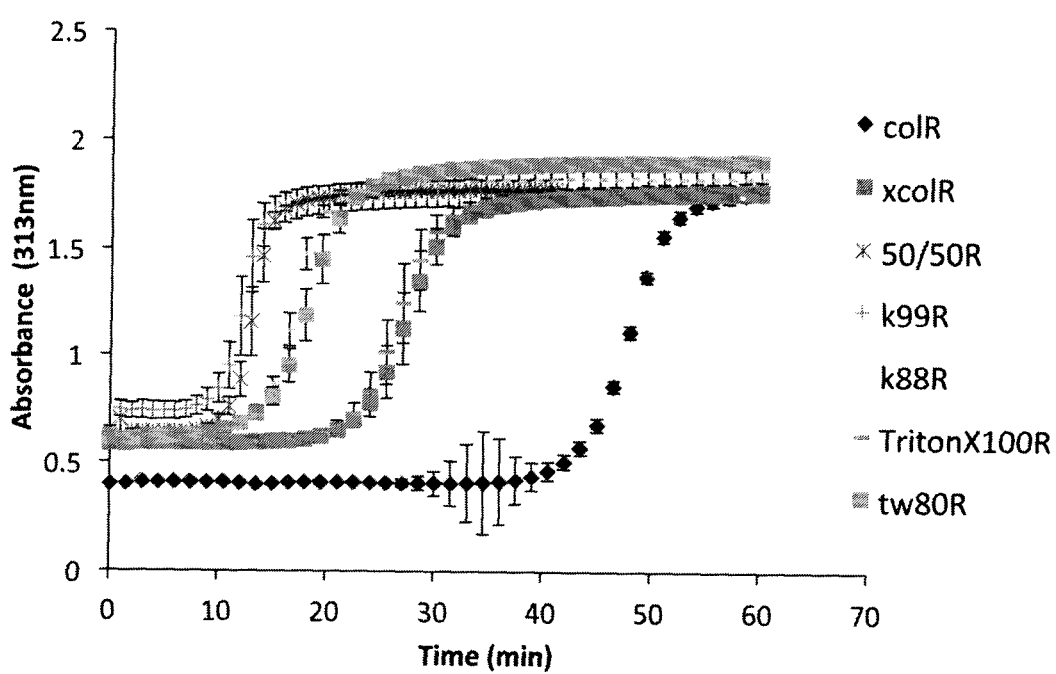

FIGURE 5
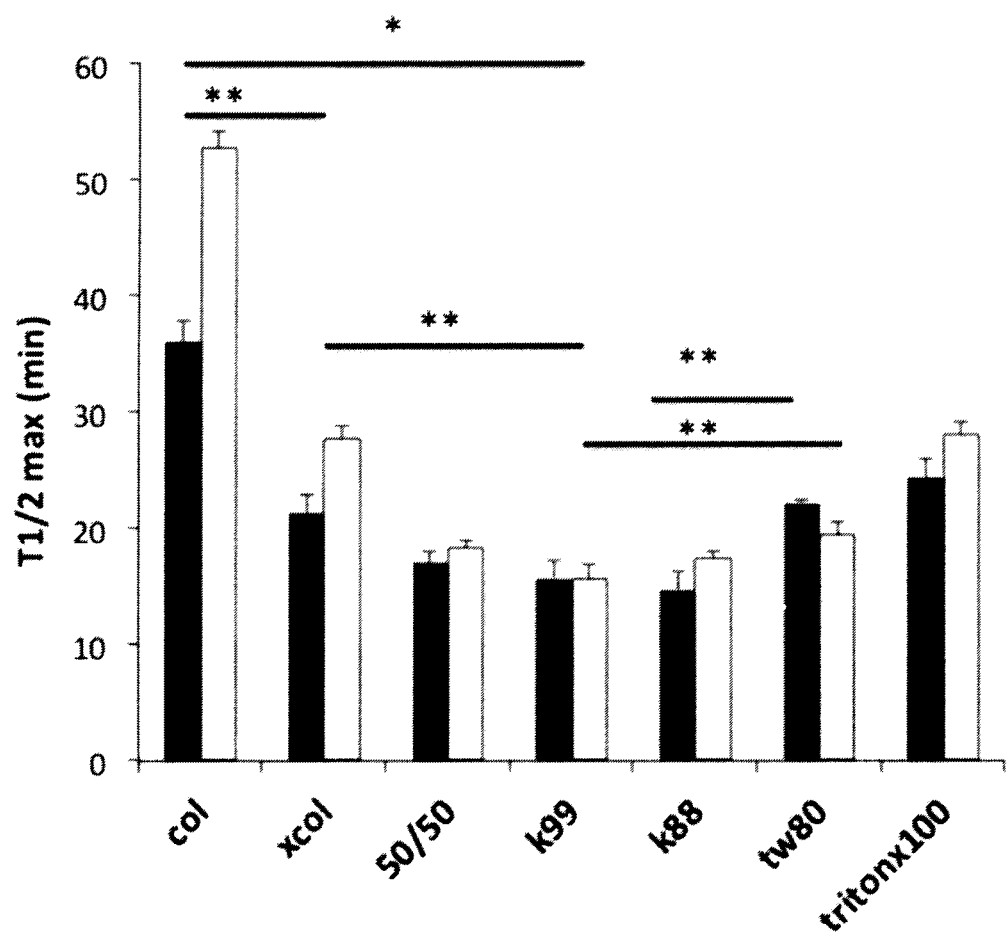
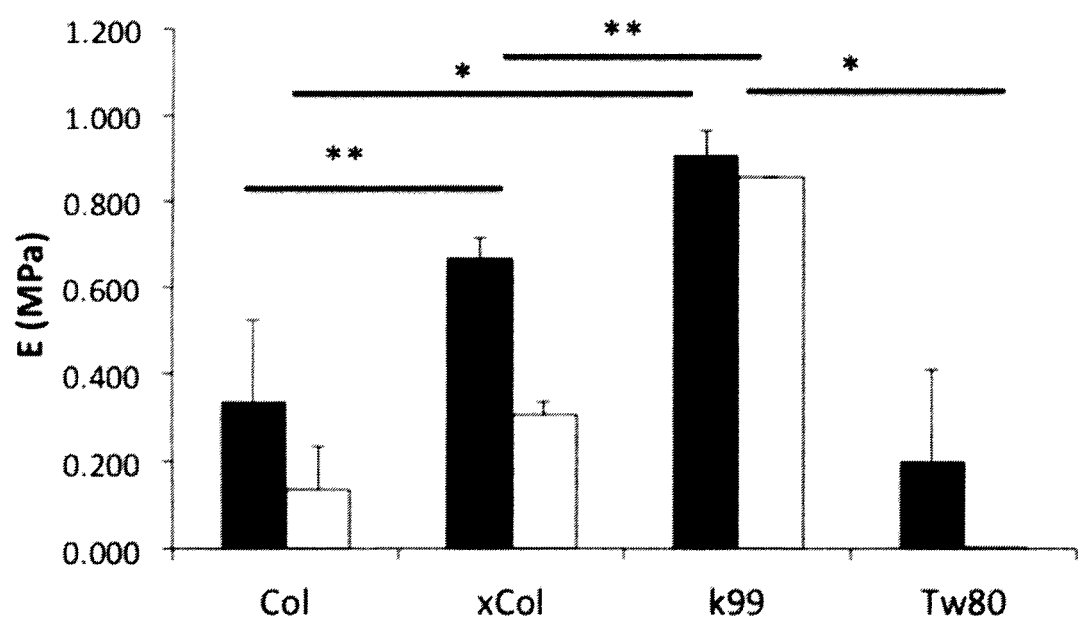

FIGURE 6
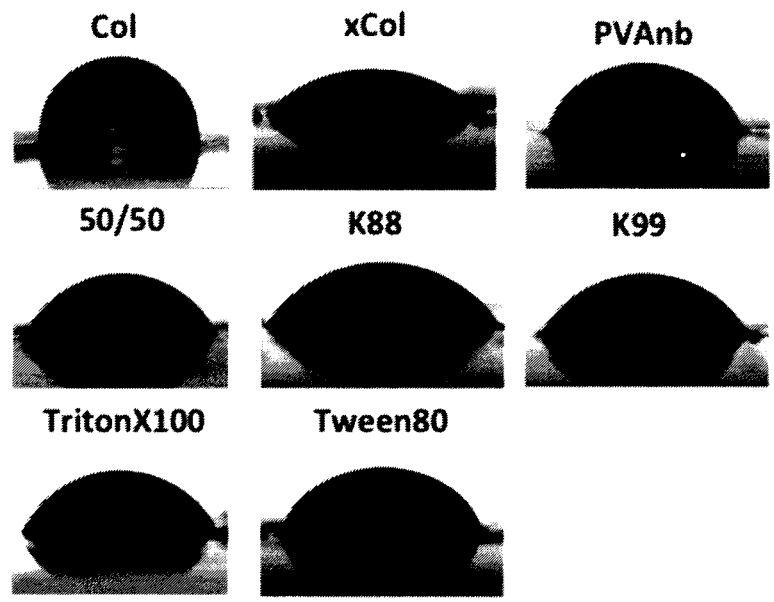
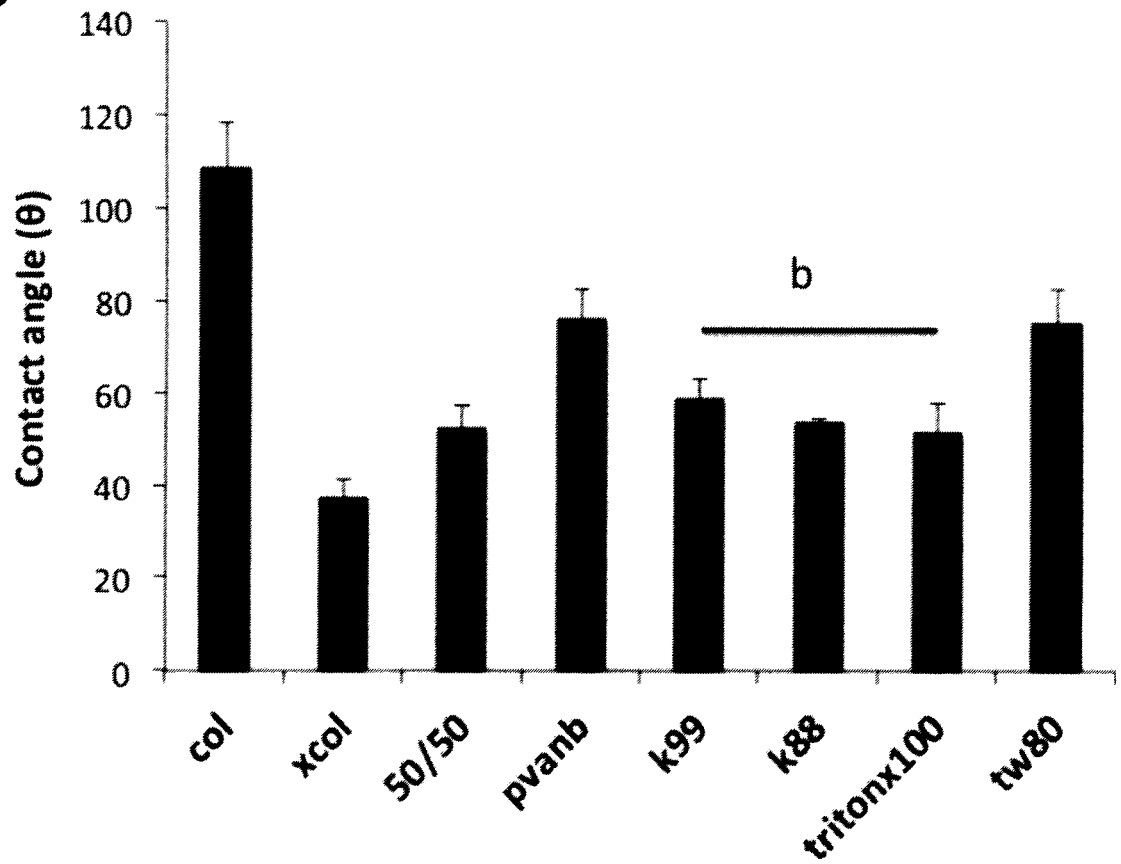

FIGURE 7
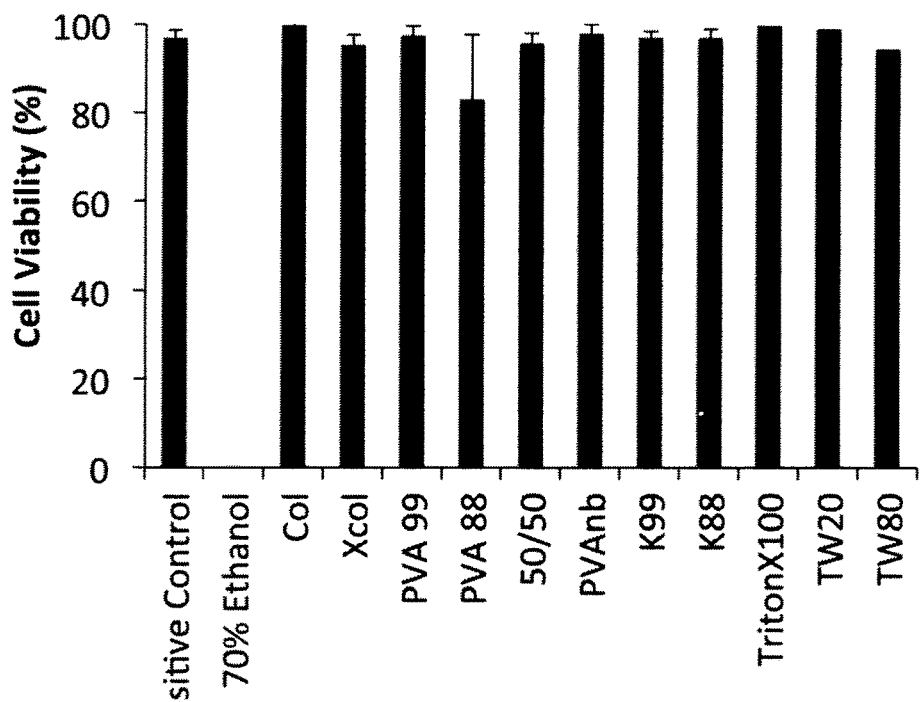
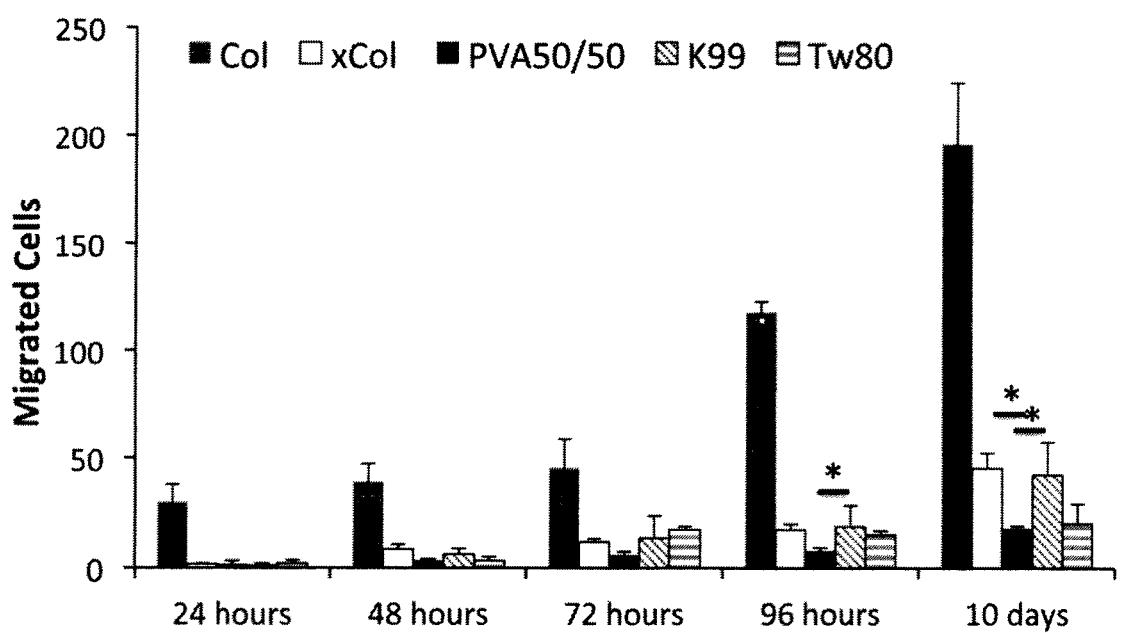

FIGURE 8
Col
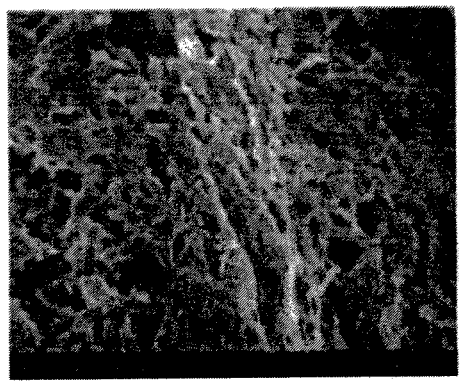 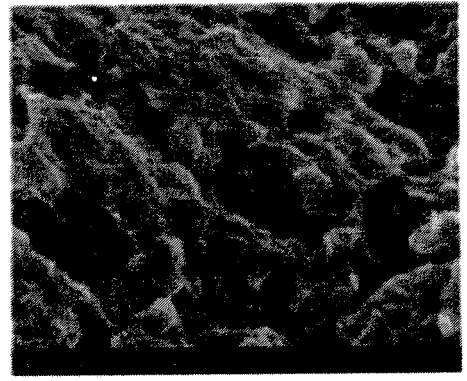
xCol
 
Tw80
 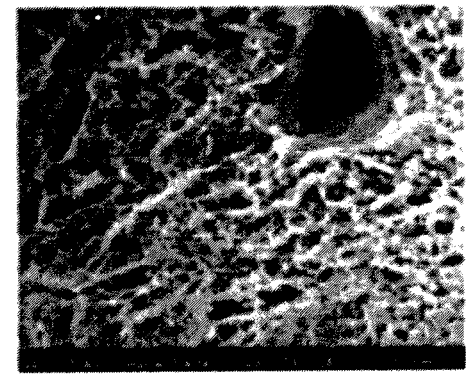
K99
 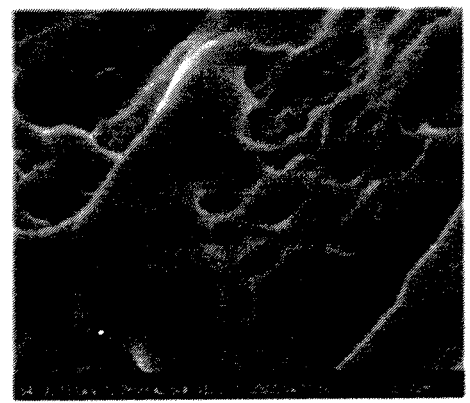

FIGURE 10
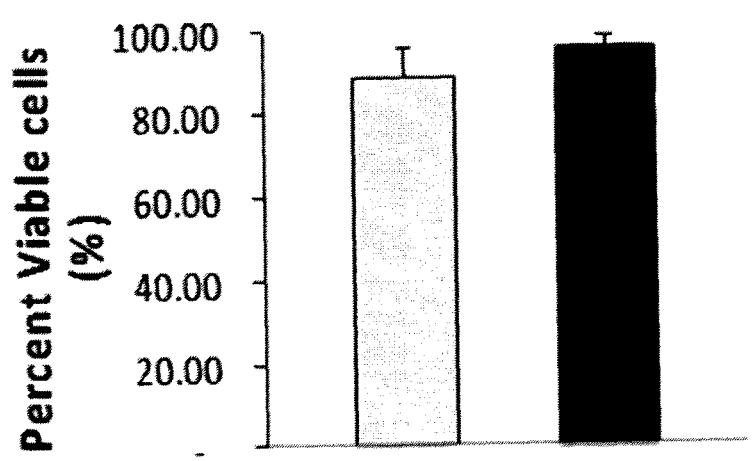

ENGINEERED TISSUE SUBSTITUTE SYSTEM

CROSS REFERENCE TO RELATED APPLICATIONS

This application claims the benefit of U.S. Provisional Patent application Ser. No. 62/112,883 filed on 6 Feb. 2015, entitled "ENGINEERED TISSUE SUBSTITUTE SYSTEM".

TECHNICAL FIELD

The present invention relates to wound healing, tissue engineering, cell transplantation and polymer science. In particular, the invention relates to tissue and matrix substitute compositions, methods of use and methods of making thereof. The present invention further provides methods of use include methods of wounds healing and cell transplantation.

BACKGROUND

Wound care transcends age, sex, nationality and other demographics, and is a costly segment of health care, valued at $16 billion worldwide. Despite the fact that current wound care products are highly innovative, complicated wound healing may still lead to prolonged and reoccurring hospital stays and amputations. Major diseases such as obesity and diabetes, together with an aging population, are among the driving forces behind the prevalence of complicated wounds. The normal healing cascade of acute wounds consists of clotting, re-epithelialization, and then remodeling of the newly formed tissue. Complicated wounds, such as chronic wounds (ulcers) or burns, can remain open due to cellular and/or physiological healing deficits. The longer a wound remains open the greater the chance of infection and bioburden (biofilms), and often the greater the risk of scarring. The advanced wound care industry has, for these reasons, a tremendous amount of interest in developing more effective biological wound dressings. One strategy for tissue repair and regeneration is the use of biomimetic scaffolds that foster the growth and development of a tissue toward restoring its normal architecture. One major problem with solid (sheet) scaffolds is their inability to conform to wounds of irregular shapes and sizes. Where injectable materials may be useful, current commercially available materials are weak in comparison to surrounding tissue. Nonetheless in situ gelling extracellular matrices can improve the performance of cell transplant and other surgical procedures.

Numerous advances in the polymer sciences to have provided many options for further developments (for example, U.S. Pat. No. 7,799,767, 7,226,611, 6,833,408, 6,818,018, 6,136,334, 5,147,344, 4,664,857, 4,565,784, WO2000/061660, WO1999/053968, E J. Suuronen et al. Toxicological Sciences (2004) and B. Sarti, M. Scandola Biomaterials (1995) and Rémi Parenteau-Bareil et al. Materials (2010)). Furthermore, R. Hartwell et al. describe a hydrogel-collagen composite that improved characteristics (Acta Biomaterialia (2011)). Nevertheless, there is a significant and currently unmet need for improved wound care strategies, products and approaches.

SUMMARY

The present invention is based, in part, on the surprising discovery that certain compositions comprising collagen, glycosoaminoglycan, hydrogel and one or more cross-linkers, is capable of forming a strong, thermally and enzymatically stable matrix suitable for a variety of uses. Some embodiments of the invention are further based on the fortuitous discovery that such compositions are able to be prepared in a dry powdered form which may be reconstituted with a suitable solvent, including a physiological fluid (for example, blood serum or plasma), to form a strong, thermally stable matrix. Embodiments of the invention are further based on the discovery that such compositions may find particular utility as a therapeutic for treatment of wounds and cell transplantation in general. Embodiments of the invention are further based on the fortuitous finding that cells respond favorably to some of the composition described herein, which is distinctly different than previously known compositions of collagen and glycosaminoglycan alone.

In a first embodiment, there is provided a composition, the composition including: (a) collagen, wherein the collagen is at a concentration of between 2-10 mg/ml; (b) glycosaminoglycan, wherein the ratio of the glycosaminoglycan to collagen is a weight ratio from about 4:1 to about 8:1; (c) a biocompatible small molecule cross-linker of collagen and glycosaminoglycan; (d) a hydrogel, wherein the hydrogel is 0.3%-1.2% w/vol of the final composition; and (e) a biocompatible, small-molecule, hydrogel cross-linker.

In a further embodiment, there is provided a composition, the composition including: (a) collagen, wherein the collagen is at a concentration of between 2-10 mg/ml; (b) glycosaminoglycan, wherein the ratio of the glycosaminoglycan to collagen is a weight ratio from about 4:1 to about 8:1; (c) a hydrogel, wherein the hydrogel is 0.3%-1.2% w/vol of the final composition; and (d) a biocompatible, small-molecule, hydrogel cross-linker.

In a further embodiment, there is provided a composition, the composition including: (a) collagen, wherein the collagen is at a concentration of between 2-10 mg/ml; (b) glycosaminoglycan, wherein the ratio of the glycosaminoglycan to collagen is a weight ratio from about 4:1 to about 8:1; (c) a hydrogel, wherein the hydrogel is 0.2%-1.2% w/vol of the final composition; and (d) a biocompatible, small-molecule, hydrogel cross-linker.

In a further embodiment, there is provided a composition, the composition including: (a) collagen, wherein the collagen is at a concentration of between 2-10 mg/ml; (b) glycosaminoglycan, wherein the ratio of the glycosaminoglycan to collagen is a weight ratio from about 4:1 to about 8:1; (c) a hydrogel, wherein the hydrogel is 0.1%-1.2% w/vol of the final composition; and (d) a biocompatible, small-molecule, hydrogel cross-linker.

In a further embodiment, there is provided a lyophilized composition, the composition including: (a) collagen, wherein the collagen is at a concentration of between 3-10 mg/ml; (b) glycosaminoglycan, wherein the ratio of the glycosaminoglycan to collagen is a weight ratio from about 4:1 to about 8:1; (c) a biocompatible small molecule cross-linker of collagen and glycosaminoglycan; (d) a hydrogel, wherein the hydrogel is 0.1%-1.0% w/vol of the final composition; and (d) a biocompatible, small-molecule, hydrogel cross-linker.

In certain embodiments, the composition is prepared as such that the collagen, glycosaminoglycan and hydrogel form a cross-linked matric as described herein, but is them subsequently lyophilized and/or powdered. In embodiments, where the lyophilized product is sufficiently small there may be no need to powder the lyophilized composition. Lyophilization may be of benefit to increase composition stability and also permits reconstitution with a solvent most suitable for the particular use.

In a further embodiment, there is provided a wound treatment method, the method including administration of a composition described herein.

In a further embodiment, there is provided a wound treatment method, the method including, reconstituting the powdered composition described herein in a solvent and administration of the reconstituted composition to a patient in need thereof.

In a further embodiment, there is provided a tissue engineering or cell transplantation method, the method including administration of a composition described herein.

In a further embodiment, there is provided a method of preparing a composition, the method including: (a) mixing collagen with glycosaminoglycan, wherein the ratio of the glycosaminoglycan to collagen may be a weight ratio from about 4:1 to about 8:1; (b) cross-linking of collagen and glycosaminoglycan; (c) adding a hydrogel to the cross-linked collagen and glycosaminoglycan, wherein the hydrogel may be 0.3%-1.0% w/vol of the final composition; and (d) cross-linking the hydrogel.

In a further embodiment, there is provided a method of preparing a composition, the method including: a) mixing collagen and glycosaminoglycan with one or more cross-linkers to cross-link the collagen and glycosaminoglycan; b) adding hydrogel polymers into the mixture from a); and c) adding cross-linker to crosslink the hydrogel within the collagen and glycosaminoglycan matrix. The method may include polymerization by heating.

In a further embodiment, there is provided a method of preparing a composition, the method including: a) cross-linking of collagen and chondroitin-6-sulfate near neutral pH; b) adding polyvinyl-alcohol based polymer hydrogel; c) adding borate and Ascorbic acid; d) freezing the mixture from c); e) drying the frozen mixture; and f) grinding the freeze dried product into a powder.

In a further embodiment, there is provided a product obtained by the method described herein.

In a further embodiment, there is provided a commercial package, including: (a) a composition described herein; and (b) a container.

In a further embodiment, there is provided a use of a composition described herein in the manufacture of a medicament for wound treatment.

In a further embodiment, there is provided a use of a composition described herein for wound treatment.

In a further embodiment, there is provided a method of culturing cells, including the mixing of cells with a described herein.

In a further embodiment, there is provided a method of skin grafting, the method including: (a) applying a meshed skin graft; and (b) filling interocites of the meshed skin graft with the composition or reconstituted composition described herein.

In some embodiments the composition does not have a small molecule cross-linker present since the collagen and glycosaminoglycan were crosslinked using an enzymatic, thermal or ultraviolet crosslinking methodology (i.e. transglutaminase, dehydrothermal treatment (DHT), or ultraviolet irradiation (UV)).

The compositions may also contain trace amounts of dextran where used to stabilize the glutaraldehyde cross linking reaction, as a non-reducable sugar that may also provide osmotic balance. Non-borate/non-PVA hydrogels may work with a higher weight percentage, but as the PVA/borate hydrogel weight percentage increases above 0.1% it may become more difficult to handle. Concentrations up to 1% w/v, work well enough but may have slowed cell growth. A suitable range may be 0.01-0.5%. Other than glycosaminoglycans, unbranched polysaccharides may be used, but non-sulfated polysaccharides are not advised (for example, hyaluronic acid). Also, chitosan and hyaluronan are not to be used.

The collagen may be primarily fibrillar collagen. The fibrillar collagen may be selected from one or more of collagens Type I, II, III, V and XI. The fibrillar collagen may be Type I collagen. The collagen may be at a concentration of between 3-10 mg/ml. The ratio of the glycosaminoglycan to collagen may be a weight ratio from about 5:1 to about 8:1. The ratio of the glycosaminoglycan to collagen may be a weight ratio of 6:1. The glycosaminoglycan may be a sulfated glycosaminoglycan. The glycosaminoglycan may be selected from one or more of the following: dermatan sulfate, keratan sulfate, heparan sulfate and heparin. The glycosaminoglycan may be chondroitin 6-sulfate.

The biocompatible small molecule cross-linker of collagen and glycosaminoglycan may be selected from one or more of the following: glutaraldehyde, 1-ethyl-3-(3-dimethylaminopropyl) carbodiimide (EDAC), EDC (1-Ethyl-3-(3-dimethylaminopropyl)-carbodiimide):NHS (N-hydroxysuccinimide), EDC (1-Ethyl-3-(3-dimethylaminopropyl)-carbodiimide):sulfo-NHS (N-hydroxysulfoxuccinimide), hexamethylene diisocyanate and Genipin. The biocompatible small molecule cross-linker of collagen and glycosaminoglycan may be glutaraldehyde or Genipin. The biocompatible small molecule cross-linker of collagen and glycosaminoglycan may be glutaraldehyde. The biocompatible small molecule cross-linker of collagen and glycosaminoglycan may be Genipin.

The hydrogel may be formed from hydrogel polymers and hydrogel polymers are selected from one or more of: polyvinyl alcohol (PVA); polyvinyl acetate (PVacetate); thiolated polyvinyl alcohol; polyvinyl alcohol block polymers containing polyethylene glycol (PVA-PEG); polyvinylpyrrolidone (PVP); and a copolymer thereof of any two or more of the preceding polymers. The hydrogel polymer may be PVA. The hydrogel polymer may be PVA-PEG. The hydrogel polymer may be PVacetate. The hydrogel polymer may be PVP. The hydrogel polymer may be thiolated polyvinyl alcohol. The hydrogel may be 0.3%-1.0% w/vol of the final composition. The hydrogel may be 0.01-0.5% w/vol of the final composition. The hydrogel may be 0.4%-0.8% w/vol of the final composition. The hydrogel may be 0.4%-0.7% w/vol of the final composition. The hydrogel may be 0.4%-0.6% w/vol of the final composition. The hydrogel may be 0.5%-0.6% w/vol of the final composition. The hydrogel may be 0.4%-0.5% w/vol of the final composition. The hydrogel may be 0.01-1.5% w/vol of the final composition.

The biocompatible, small-molecule, hydrogel cross-linker may be 0.01% (w/v)-0.0001% (w/v) of the final composition. The biocompatible, small-molecule, hydrogel cross-linker may be 0.01% (w/v)-0.1% (w/v) of the final composition. The biocompatible, small-molecule, hydrogel cross-linker may be sodium borate decahydrate. The biocompatible, small-molecule, hydrogel cross-linker may be sodium borate decahydrate.

The composition may further include a solvent. The solvent may be water or a physiological fluid. The physiological fluid may be blood, serum or plasma. The solvent may be media. The media may be cell media.

The matrix formed by gelation of the composition has a tensile strength of between 0.2-2.0 MPa. The matrix formed by gelation of the composition has a tensile strength of between 1.45-2.0 MPa. The composition described herein, wherein fibrillogenesis begins within 13-16 minutes of solvent addition. The composition described herein, wherein gelation of the powder occurs between 25°-40° C. The composition described herein, wherein gelation of the powder occurs between 25°-37° C. The composition described herein, wherein gelation of the powder occurs between 30°-37° C. The composition described herein, wherein gelation of the powder occurs at 37° C.

The cross-linking of collagen and glycosaminoglycan may be by dehydrothermal treatment (DHT), ultraviolet irradiation (UV) or enzymatic crosslinking. The cross-linking of collagen and glycosaminoglycan may be by small molecule cross-linker of collagen and glycosaminoglycan. The cross-linker of collagen and glycosaminoglycan may be selected from one or more of the following: glutaraldehyde, 1-ethyl-3-(3-dimethylaminopropyl) carbodiimide (EDAC), EDC (1-Ethyl-3-(3-dimethylaminopropyl)-carbodiimide): NHS (N-hydroxysuccinimide), EDC (1-Ethyl-3-(3-dimethylaminopropyl)-carbodiimide):sulfo-NHS (N-hydroxysulfoxuccinimide), hexamethylene diisocyanate and Genipin. The cross-linker of collagen and glycosaminoglycan may be glutaraldehyde. The cross-linker of collagen and glycosaminoglycan may be Genipin. The method may further include adding dextran.

The method may further include lyophilizing of the composition. The method may further include powdering the lyophilized composition. The method may further include reconstituting the powder in a solvent. The solvent may be a physiological fluid or water. The physiological fluid may be blood, serum or plasma.

The method may further include adding an aqueous biological or non-biological solvent to the powder to form a reconstituted composition. The method may further include adjusting the viscosity of the reconstituted composition. The method may further include adjusting of the viscosity may be with a shear-thinning agent. The shear-thinning agent may be guar gum. The adjusting of the viscosity may be with a shear thickening agent. The shear-thickening agent may be dextran. The method may further include the addition of cells to the reconstituted composition. The cells may be autologous, allogeneic or xenogeneic cells.

The composition may be a lyophilized powder. The commercial package may further include one or more of: (a) a solvent; (b) a syringe; (c) a needle; and (d) a PDMS thin film. The PDMS thin film may be used as a dressing, but alternative dressings may also be included in the commercial package.

The commercial package may further include a syringe with a mixing valve.

The cells may be selected from one or more of: adipocytes; adult regenerative cells; Schwann cells; skin derived neuronal progenitor cells; DRCs; and ASCs.

The compositions described herein have also been evaluated against matrigel in a non-healing wound mouse model, and found it to promote wound healing faster than matrigel.

Certain embodiments have PVA hydrogels at 0.4%-1.2% w/vol of the final composition. Certain embodiments have PVA hydrogels at 0.8%-1.0% w/vol of the final composition where PVA-PEG block copolymer is used. Other embodiments have PVA hydrogels at 0.4%-0.6% w/vol of the final composition fortuitous showed that a viscous solution that would gel at a lower temperature than 37° C. was possible. Furthermore, this concentration was more suitable for sustaining viable cells. Additionally, it was shown that embodiments where the PVA (pH 7.0) PVA was 10% (w/v) and comprises a mixture (50/50) of high molecular weight PVA (125 kD-200 kD) that is 99% hydrolyzed and medium molecular weight PVA (40 kD-100 kD) that is only 88% hydrolyzed ("% hydrolyzed" refers to the percentage of hydrolyzed acetate groups into alcohols) (10% HMW/MMW 50/50 99% hyd/88%) was preferred in certain embodiments.

Certain embodiments have polyvinyl alcohol (PVA) hydrogels and variants thereof (for example, thiolated polyvinyl alcohol; polyvinyl alcohol block polymers that contain polyethylene glycol (PVA-PEG); or a copolymer thereof) were used were found to benefit from the use of sodium borate decahydrate as the biocompatible small molecule cross-linker of the hydrogel. A concentration of sodium borate decahydrate (pH 8) between 0.02% (w/v)-0.0001% (w/v) of the final composition may be used. Furthermore, a concentration of sodium borate decahydrate (pH 8) between 0.01% (w/v)-0.0001% (w/v) of the final composition was fortuitously found to provide a more stable gel than PVA gels with higher concentrations of borate. Some gels, with higher than 0.03% concentrations of borate, when the PVA content is relatively high may prematurely gel, the optimal ranges (i.e. 0.02% (w/v)-0.0001% (w/v) of the final composition) make gel handling easier during fabrication (for example, would provide a more uniform mix). In experiments with the PVA hydrogels, it was noticed that addition of PVA and mixing into the collagen-glycosaminoglycan scaffold prior to adding borate, is favourable as it produces an interpenetrating-like hydrogel formation that is afterward complexed or crosslinked by borate in and around collagen (or by observation—a more viscous, homogenous collagen mixture).

In certain embodiments, where the addition of one or more cross-linkers post collagen-GAG-hydrogel matrix fabrication were fortuitously found to add adhesive properties to the gel matrix. In particular the addition of Genepin (3.5-5.0 μM) and/or Transglutaminase (1-3U) have been found to be useful in this regard.

Some embodiments are further based on the fortuitous discovery that compositions described herein may be further lyophilized following matrix formation. It was discovered that the lyophilized composition could further be powdered. Surprisingly, it was found that the lyophilized powdered compositions have improved stability, which has benefits for ease of use and packaging. Furthermore, not only could the powdered lyophilized composition be reconstituted with water, but also with a patient's whole blood, serum or plasma before use in wound healing etc. Fortuitously, the powdered lyophilized composition once reconstituted still formed gels using water, whole blood, serum and plasma. Furthermore, the use of blood or blood components may provide a nutrient rich solvent to benefit the wound healing process.

Provided herein are novel multicomponent tissue substitute system, including compositions and methods of use, embodiments of which have advantages over available wound care products.

In certain aspects, there is provided an engineered tissue substitute composition comprising collagen, glycosaminoglycan, a hydrogel, and one or more cross-linkers. In certain embodiments, the engineered tissue substitute composition comprises a mixture of Type I collagen, sulfated glycosamino-glycan, poly-vinyl alcohol borate hydrogels, glycerol and ascorbic acid. In certain embodiments, the glycosaminoglycan is hyaluronic acid. In certain embodiments, the hydrogel is polyvinyl alcohol, polyvinyl acetate, thiolated polyvinyl alcohol, or a co-polymer thereof. In certain embodiments, the one or more cross-linkers is selected from the following: gluteraldehyde, EDC:NHS, borate. In certain embodiments, the composition exists in a dry form. In other embodiments, the composition exists in a polymerized form. In other embodiments, the composition further comprises a solvent such that the composition exists primarily in a liquid, unpolymerized form. In certain embodiments, the liquid form may be transformed into a polymerized form by heating the composition. In certain embodiments, the dry form may be reconstituted by addition of a suitable solvent. The suitable solvent may be a physiological fluid, for instance blood, serum, plasma, and the like, or the suitable solvent may be a non-physiological fluid, for instance water.

In certain aspects, there is provided a method of treatment of a wound in a subject requiring such treatment, the method comprising administering to the subject the engineered tissue substitution composition described herein. In certain embodiments, the wound may be as a result of, but is not limited to, injury, burns, surgical procedures, infection and ulcers.

In certain aspects, there is provided a method of preparation of an engineered tissue substitute composition, comprising mixing collagen, glycosaminoglycan, a hydrogel, and one or more cross-linkers in a suitable solvent. In certain embodiments, the mixed composition will remain in a non-polymerized form until heated above room temperature. In certain embodiments, the composition is subsequently dried to remove solvent, allowing preparation of a dry form. The composition may be subsequently reconstituted back into a liquid form, using a suitable solvent such as a physiological fluid, or water. In certain embodiments: 1) the collagen and glycosaminoglycan are first mixed with one or more cross-linkers to allow some cross-linking between these components; 2) the hydrogel polymers are added to the collagen-glycosaminoglycan and then mixed with one or more cross-linkers, such as borate, to allow some cross-linking of these components; and 3) the mixtures of step 1) and 2) are mixed in a suitable solvent. The composition may then be polymerized by heating.

DESCRIPTION OF THE DRAWINGS

FIG. 1 shows a flow diagram of the process for the fabrication of the reconstitutable collagen scaffold, wherein steps 1-8 describe the process by which one can manufacture the scaffold, freeze-dry, then reconstitute using water or other aqueous media and easily apply to a wound bed or cell culture container.

FIG. 2 shows plots of the effect of cross-linker concentration on fibril formation kinetics and turbidity, wherein the collagen solutions (3 mg/ml) were fabricated either in the absence (Col) or presence of glutaraldehyde cross-linker and collagen solutions were maintained on ice until being placed in a TECAN™ spectrophotometer at 37° C. to measure turbidity as an indicator of fibril formation (gelation) at 313 nm, with Panel (A) depicting collagen fibril formation kinetic profiles of three conditions described in TABLE 1 and Panel (B) depicts a third condition with collagen alone as a control (col), where the glutaraldehyde concentration is the same as C1 in panel A (0.002% wt) and the incubation time is proportional to the reaction volume and the "60 min Voleq" solution has a reaction concentration of collagen at 1.5 mg/ml, whereas the other two solutions contain 3 mg/ml collagen.

FIG. 4 shows plots of the effect of PVA variants on collagen fibrillogenesis pre- and post lyophilization/reconstitution, where collagen solutions of (3 mg/ml) alone (col) or crosslinked and combined with hydrogels or surfactants as follows: (xcol) crosslinked without any additives, (50/50) 50% PVA88/50% PVA99, (K99) 50% Kollicoat™/50% PVA99, (K88) 50% Kollicoat™/50% PVA88, (tritonx100) TritonX-100™, (tw80) Tween 80™, where panel (A) depicts the shift in t½ max for collagen fibrillogenesis with the addition of cross-linker, surfactant and PVA-hydrogel combination and panel (B) depicts the fibrillogenesis of lyophilized and reconstituted collagen solutions matched to panel (A) and denoting the shifts in t½ max, with the exception of k99, k88 and 50/50.

FIG. 5 shows bar graphs quantifying collagen solution gelation kinetics and mechanical properties pre- and post lyophilization (freeze drying), where panel (A) shows the quantification of scaffold gelation time (fibrillation) as indicated by $t_{1/2max}$, where scaffolds were prepared as described in materials and methods and pane. (B) shows the uniaxial mechanical strength (Young's modulus, E) of scaffold variants (Bar grouping with (*) denotes a statistical significance of $p<0.001$ and (**) $p<0.05$).

FIG. 6 shows contact angle measurements of dry gelled collagen films, with the effect of additive on surface hydrophilicity/hydrophobicity (surface wettability) was investigated through contact angle calculations. Variants were prepared as described in the materials and methods. Panel (A) shows photomicrograph images of a single water drop on the collagen scaffold surface and panel (B) shows a bar graph of the calculated contact angles for scaffold variants, wherein the statistical significance of $p<0.05$ was found between all treatments, with the exception of K88, K99, TritonX100 as denoted by the bar "b". Statistical significance between the "b" group and all other treatments was observed.

FIG. 7 shows cell viability and cell migration by collagen scaffold variants, with panel (A) showing a bar graph of the viability of primary fibroblasts cultured in collagen scaffold variants following 24 hours, wherein Live/Dead ratios were utilized to calculate the percent of viable cells, using 70% ethanol as a dead control and panel (B) showing a bar graph of cell migration, wherein 4 mm punches were made in scaffolds and then refilled with an acellular scaffold variant, whereby cells were counted as they migrated from the old scaffold into the new scaffold over a period of ten days (cell numbers represent the total number of cells counted per scaffold variant at the denoted time point).

FIG. 8 shows fibroblast morphology and collagen scaffold architecture in variants, wherein scanning electron micrographs of freeze-dried collagen scaffold variants: (col) collagen, (xcol) crosslinked collagen scaffold without additives, (Tw80) crosslinked collagen scaffold with Tween 80™ additive, and (K99) crosslinked collagen scaffold with Kollicoat™/PVA99 additive (Left panel scale bar: 100 um and right panel scale bar: 20 um).

FIG. 10 shows in panel (A) the application of a sprayed composition of the reconstituded scaffold onto a partial thickness wound in pig skin, wherein the scaffold forms a thin layer gel-scaffold after spraying and in in panel (B) a bar graph of viability of primary skin cells after spraying compared with cells seeded onto culture surface show no difference in viability.

DETAILED DESCRIPTION

Figure 3:
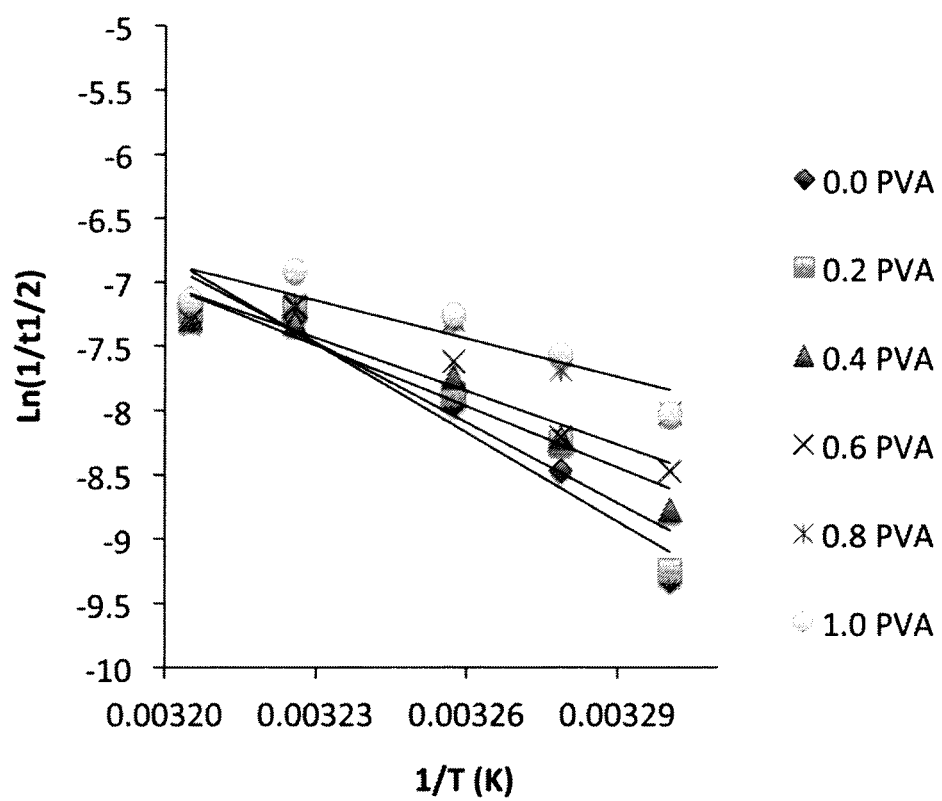
FIG. 3 shows an Arrhenius plot for collagen fibrillation as a function of PVA-borate hydrogel concentration, where non-crosslinked collagen scaffold variants were prepared as described in the materials and methods, containing 0-1.0% w/v polyvinyl alcohol (PVA) (50% wt 99% hydrolyzed and 50% wt 88% hydrolyzed). Using Equation (Nemeth and Martin, 1988) a reduction in the activation energy for collagen fibrillogenesis is observed at 313 nm as the concentration of PVA is increased.
Figure 9:
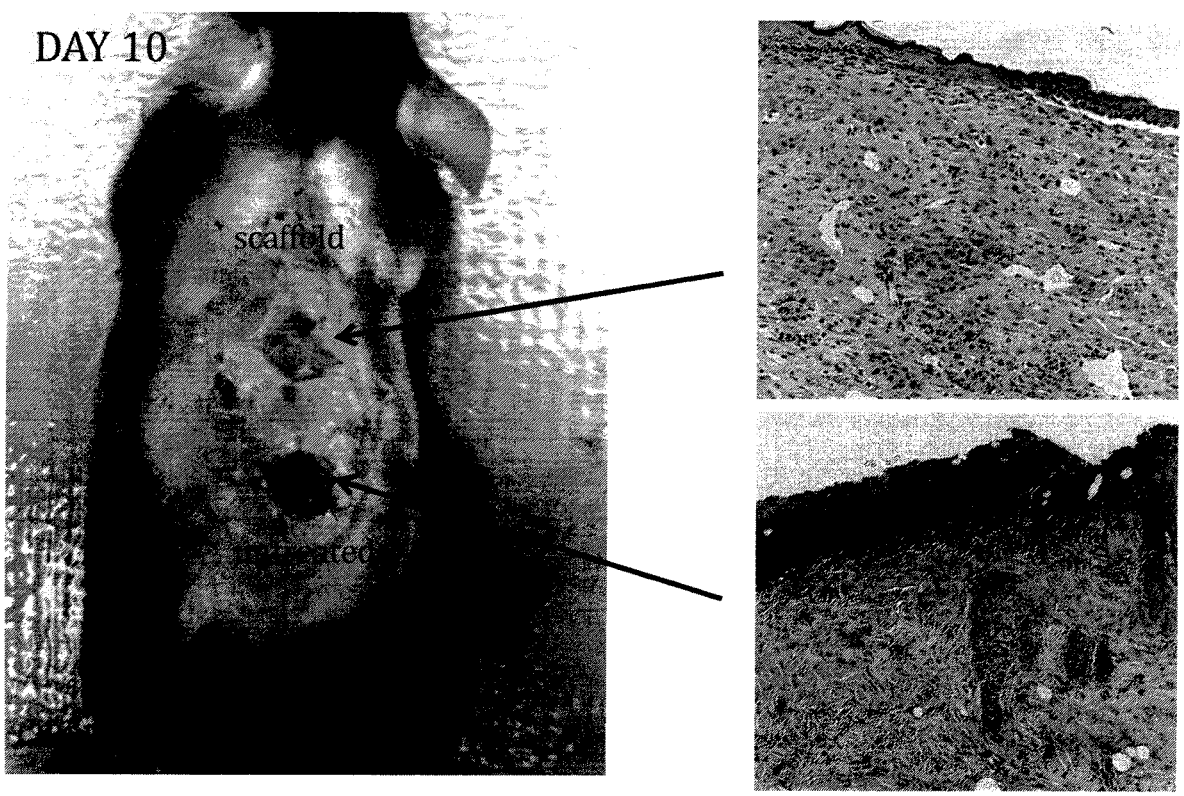
FIG. 9 shows day 10 post surgical outcomes of the biohybrid scaffold applied in non-healing (splinted) mouse wounds, wherein acellular biohybrid scaffold was reconstituted and applied to the upper wound and the bottom wound was left untreated. All wounds were covered with silicone based occlusive dressings and the clinical appearance of re-epithelization in the biohybrid treated wounds, while untreated wounds remain unhealed with scab. The top and bottom panels on the right show histological evidence of complete neoepidermal formation and granulation tissue reminance in the biohybrid treated wounds, compared with the chronic wound pathology observed in the untreated wounds (lack of epidermis and pseudo epithelial masteosis hyperplasia).

Any terms not specifically defined herein shall be understood to have the meanings commonly associated with them as understood within the art of the invention.

Definitions

The term "collagen" as used herein, is a structural protein found commonly in fibrous animal tissues and encompasses primarily fibrillar collagens (for example, Type I, II, III, V, XI), but may also include non-fibrillar collagens i.e. Type IV, VI, VII, VIII, IX, X, IX, XII, XIII, XIV, XV, XVI, XVII, and XIX. Most commonly used herein was Type I Collagen.

The term "glycosaminoglycan" (GAG) as used herein, is meant to encompasses sulfated glycosaminoglycan. For example, chondroitin sulfate; dermatan sulfate, Keratan sulfate, Heparan sulfate, Heparin. Members of the glycosaminoglycan family vary in the type of hexosamine, hexose or hexuronic acid unit they contain (e.g. glucuronic acid, iduronic acid, galactose, galactosamine, glucosamine) and they also vary in the geometry of the glycosidic linkage.

The term "biocompatible small molecule cross-linker of collagen and glycosaminoglycan" is meant to encompass any suitable cross-linker of collagen and glycosaminoglycan. For example, may include one or more of: glutaraldehyde, 1-ethyl-3-(3-dimethylaminopropyl) carbodiimide (EDAC), EDC (1-Ethyl-3-(3-dimethylaminopropyl)-carbodiimide):NHS (N-hydroxysuccinimide), EDC (1-Ethyl-3-(3-dimethylaminopropyl)-carbodiimide):sulfo-NHS (N-hydroxysulfoxuccinimide)], hexamethylene diisocyanate, and Genipin. The term may also encompass other carbodiimides or isocyanates or enzymatic crosslinkers.

The term "non-small molecule cross-linker of collagen and glycosaminoglycan" is meant to encompass any suitable non-small molecule cross-linker of collagen and glycosaminoglycan. For example, dehydrothermal treatment (DHT), ultraviolet irradiation (UV) and enzymatic cross-linking (for example, Transglutaminase). The chemical techniques used to crosslink Collagen-Glycosaminoglycan cross-linking are diverse. The use of aldehydes such as formaldehyde and glutaraldehyde are well characterized. Glutaraldehyde is the most commonly used chemical method of crosslinking collagen-based biomaterials. Alternatively, members of the carbodiimide family may also be used to enhance mechanical and enzymatic resistance of a collagen scaffold. Furthermore, these chemicals may also be used to crosslink collagen to some gold nanostructure or in combination with epoxy. Isocyanates, for example, hexamethylene diisocyanate, is known for crosslinking collagen scaffolds. The commercially available Zimmer™ Collagen Repair Patch uses a proprietary isocyanate crosslinking technique. Genipin, a chemical cross-linker derived from a vegetal source and may optionally be used instead of or in addition to glutaraldehyde in the present compositions.

As an alternative to covalent bond crosslinking as described above, the formation of ionic bonds between collagen molecules may be suitable in certain circumstances. For example, polycationic molecules such as chitosan create ionic bonds between its numerous amine groups and the carboxyl groups of collagen.

Also, enzymatic crosslinking agents like transglutaminase can be used to enhance tensile strength and enzymatic resistance of collagen-based matrices. The use of an enzymatic cross-linker, is that no chemical residues or byproducts remain in the scaffold structure.

The term "dextran" as used herein is meant to a complex branched glucan (i.e. a polysaccharide made of many glucose molecules) and may be composed of chains of varying lengths (from 3 to 2000 kilodaltons) serves to stabilize the glutaraldehyde cross linking reaction (especially the higher molecular weights), as a non-reducable sugar that can also provide osmotic balance. Depending on the reaction components and the reaction conditions, with a lack of dextran the glutaraldehyde may react far more quickly than desired. Following detran use there may be trace amounts remaining within the composition. A typical mixture of glutaraldehyde and dextran may be 6 ml of glutaraldehyde (25%) and 94 ml of dextran (20%).

The term "hydrogel" as used herein is meant to encompass a hydrophilic network of polymer chains. For example, a hydrogel may be made up of polymers of polyvinyl alcohol, polyvinyl acetate, thiolated polyvinyl alcohol, polyvinyl alcohol block polymers that contain polyethylene glycol (PVA-PEG), or a copolymer thereof, also including variants of co-polymers and partially modified forms (e.g. PVacetate, PVP and thiolated). In certain embodiments as "polyvinyl alcohol, polyvinyl acetate, thiolated polyvinyl alcohol, or a co-polymer thereof.

The term "polyvinyl alcohol borate hydrogel" as used herein refers to a PVA hydrogel where borate is used to crosslink the PVA polymers.

The term "PVA 10% HMW/MMW 50/50 99% hyd/88%" as used herein refers to a solution of PVA that is 10% (w/v) and comprises a mixture (50/50) of high molecular weight PVA (125 kD-200 kD) that is 99% hydrolyzed and medium molecular weight PVA (40 kD-100 kD) that is only 88% hydrolyzed. ("% hydrolyzed" refers to the percentage of hydrolyzed acetate groups into alcohols)

The term "biocompatible small-molecule cross-linker of the hydrogel" or "biocompatible, small-molecule, hydrogel cross-linker" is meant to encompass any suitable small molecule that is capable of linking the hydrogel polymers together. For example, for a PVA hydrogel, sodium borate decahydrate is preferable or other borate source. As an alternative to borate another divalent cation may be used.

The term "lyophilized", "lyophilisation", "lyophilization" is meant to encompass a cryodesiccation, which is a dehydration process wherein the item being lyophilized is freeze-dried. There are essentially three categories of freeze-dryers: the manifold freeze-dryer, the rotary freeze-dryer and the tray style freeze-dryer.

The term "reconstitution" or "reconstituted" as used herein refers to the addition of a suitable solvent to the lyophilized composition or lyophilized powdered composition. The solvent may be selected from water, blood, serum, plasma, media (for example cell media) or a suitable buffer. The physiological fluid (for example, blood, serum or plasma) may be taken from the subject to whom the composition is being administered to improve compatibility. The solvent may optionally include one or more additional components, such as nutrients, growth factors, drugs, cells, etc. A suitable reconstitution weight may be between 70 mg/ml-110 mg/ml of powder or lyophilized composition.

The term "bio-hybrid scaffold" as used herein refers to the composition, reconstituted composition or reconstituted powdered composition in gel form. The bio-hybrid scaffold may optionally include one or more additional components, such as nutrients, growth factors, drugs, cells, etc. as needed for the particular application.

The term "wound" as used herein, encompasses breaks in the skin, burns, surgical procedures, infection, ulcers (for example, pressure ulcers or diabetic ulcers). The compositions described herein are suitable for wound healing including chronic wounds, wherein the scaffold may be prepared at the bedside. Furthermore, where the compositions described herein may be used as a filler of the fenestrations in a meshed skin graft. Experiments conducted by the inventors show an improvement in healing rate and healing outcome. The compositions described herein may be used in 3D printing applications.

One strategy for tissue repair and regeneration is the use of biomimetic scaffolds that foster the growth and development of a tissue toward restoring its normal architecture. With or without cells, gelling extracellular matrices can improve cell transplant and other surgical procedures. As described herein the formation of a multicomponent tissue substitute system may include composition described herein. In certain embodiments the tissue substitute system is capable of being formed in situ, and in certain embodiments it is injectable. In other embodiments the tissue substitute system may be partially or completely formed ex vivo prior to application. In certain embodiments the tissue substitute system comprises a dry composition which is able to be reconstituted in situ or ex vivo.

The primary component of the tissue substitute system is a bio-hybrid scaffold. The tissue substitute system may optionally include additional components, such as nutrients, growth factors or drugs. The system may also optionally comprise Indoleamine 2,3 dioxygenase (IDO) expressing cells for cell transplantation. The tissue substitute system described herein may be useful for treatment of skin wounds (chronic and acute), but may also be relevant for use in other areas of tissue engineering and cell transplantation.

Compositions as described herein may comprise a matrix component that is prepared by combining a cross-linked collagen-glycosaminoglycan matrix with a synthetic hydrogel system. The matrix may be stored as a lyophilized powder. When hydrated the solubilized interpenetrating polymer network that results forms a gel scaffold when heated, due in part to rapid fibril formation and extensive hydrogen bonding. Once formed, bio-hybrid scaffolds naturally assume an architecture that is similar to native dermis which is able to mitigate cellular contracture, enzymatic degradation and cellular proliferation. In certain embodiments, the composition may be present in a dry powder form. The dry powder composition may be solubilized, and thus reconstituted, with a physiological fluid, for instance whole blood, serum, or plasma, in effort to create a growth factor enriched environment. Alternatively the dry powder composition may be reconstituted with other suitable solvents, such as distilled water. In certain embodiments, the dry powder composition is reconstituted in situ. In other embodiments, the dry powder composition is reconstituted ex vivo. In other embodiments, the dry powder composition is reconstituted in vitro, for instance in a tube or other container. In various embodiments, the composition may be present in a non-dry form, for instance as a solubilized fluid, or as a partially or completely polymerized gel.

Physically the tissue substitute systems described in the present application, comprise compositions described herein, which are more thermally stable than simple cross-linked collagen injectable gels, with greater mechanical strength. This is evident by the differential scanning calorimetry, which demonstrates that the polymers within the hydrogel network improve the thermal stability of the collagen bundles. The polymers in the hydrogel are amphipathic and thus can complex, as a surfactant would, with the collagen therein improving stability. When combined with cells that express the enzyme IDO, cellular dermal scaffolds can be fabricated in-situ within minutes, which is significantly advantageous over existing dermal substitute systems.

In certain embodiments, the composition described herein may comprise the following components: collagen, glycosaminoglycan, a hydrogel, and one or more cross-linkers. In certain embodiments, collagen comprises Type I collagen that is present at a concentration between 3.0-10.0 mg/mL. In other embodiments, collagen further comprises other types of collagen (but not limited to) Type II, II, IV, V, and are present at a final concentration between 0.5-4.0 mg/ml. In certain embodiments, the glycosaminoglycan is present at a ratio of 1:6 w/w glycosaminoglycan:collagen. In certain embodiments, the glycosaminoglycan is chondroitin sulphate at a ratio of 1:6 the weight of collagen, but may also employ dermatin sulphate at a 1:6 ratio or hyaluronic acid at 0.5-1% w/vol (final concentration). In certain embodiments, the hydrogel is polyvinyl alcohol (PVA), polyvinyl acetate, polyvinyl alcohol-co-polyethylene glycol, thiolated polyvinyl alcohol, or any other co-polymer thereof. In certain embodiments, the hydrogel is present at a concentration of 0.1-1% w/v of the final composition. In certain embodiments, the hydrogel further comprises ascorbate at a concentration of 50-150 uM, and/or glycerol at a concentration of 0.01-0.1% w/v of the final composition. In certain embodiments, the one or more cross-linkers comprises gluteraldehyde and/or ethyl(dimethylaminopropyl)-carbodiimide:N-hydroxysuccinimide (EDC:NHS) specifically in a high-molecular weight dextran solution (pH 7.5-8), which is suitable for cross-linking collagen. In other embodiments, the one or more cross-linkers comprises sodium borate at a concentration of 0.1-1% w/v of the final composition, preferentially at 1:4 w/w of the polyol, which is suitable for cross-linking hydrogel.

As previously described, the compositions described herein include embodiments where the different components of the composition are mixed together as dried, or lyophilized, components in such a way that the components exist in an unpolymerized form. In other embodiments, the composition exists in a polymerized form. The polymerized form of the composition may be created by mixing of liquid solutions containing individual components, with the resulting chemical reaction creating the polymerized composition. In other embodiments, the polymerized form of the bio-hybrid scaffold composition may be created by reconstitution of the dried, or lyophilized, composition, wherein solubilization of the dry composition comprising collagen, glycosaminoglycan, hydrogel, and one or more cross-linker components causes formation of the polymerized form of the composition, such polymerization occurring as a result of cross-linking of the collagen, glycosaminoglycan, and hydrogel components caused by the one or more crosslinkers present in the composition. The one or more cross-linkers facilitate cross-linking (or polymerization) of the collagen, glycosaminoglycan, and hydrogel components upon contact with a sufficient amount of a suitable solvent, for instance a physiological fluid, water, or other suitable solvent.

In certain embodiments, the composition is provided in a partially cross-linked form, wherein the collagen and glycosaminoglycan are previously cross-linked using a suitable cross-linker such as gluteraldehyde and/or EDC:NHS, and the hydrogel is previously cross-linked using a suitable cross-linker such as sodium borate. In this partially cross-linked form, wherein there is no significant cross-linkage of the collagen:glycosaminoglycan component with the hydrogel component, the composition remains in a viscous, essentially liquid form, suitable for application, for instance to a wound. Heating of the composition will then allow further cross-linking (or polymerization) among and between the collagen:glycosaminoglycan component and the hydrogel component, catalysed by the one or more cross-linking reagents, and the composition will assume a more solid gel.

In certain embodiments, the composition is prepared by mixing non-crosslinked polymer components, collagen, glycosaminoglycan and polyols within a concentrated 10× buffer composition of ⅓ HEPES, ⅓ PBS, and ⅓ DMEM or variation of the same vitamin, nutrient, glucose and mineral enriched resuscitation fluid. Following all methods of cross-linking, and prior to freeze-drying, ascorbic acid is added to the mixture in the range of 1-1000 uM.

In certain embodiments, the composition is present in a dry form and comprises lyophilized components in quantities sufficient to allow the reconstituted, polymerized composition to have specific desirable qualities, upon addition of a sufficient quantity of a suitable solvent. In other embodiments, the composition is present in a polymerized form exhibiting certain advantageous physical properties. In certain embodiments, the reconstituted or polymerized composition may be resistant to enzymatic degradation by collagenase. In certain embodiments, the reconstituted or polymerized composition may exhibit a tensile strength of 0.2-2.0 MPa, most commonly 1.45-2.0. In certain embodiments, the dry composition may form collagen fibres within 13-16 minutes of adding a sufficient quantity of a suitable solvent. In certain embodiments, the reconstituted or polymerized composition is capable of regulating cellular proliferation, promoting linear cellular proliferation, and resisting cell-mediated matrix contraction.

As used herein, 'dry form' means essentially free of solvent, such that there is insufficient solvent present in the composition to cause chemical cross-linking of the individual components. It is understood that the dry form of the composition may still contain minute or trace amounts of solvent, however these amounts are sufficiently small that they will not cause any significant amount of chemical cross-linking of the composition. Individual components may be mixed and then the mixed composition may be dried, or alternatively, individual components may be first dried and then mixed. Drying may be accomplished by any number of means known in the art, for instance lyophilisation, freeze drying, and the like. In certain embodiments, the dry form of the bio-hybrid composition will achieve gelation upon addition of sufficient quantities of a suitable solvent, when exposed to temperatures between 25-40° C., preferable between 25-37° C., more preferably between 30-37° C., and most preferably at 37° C.

In various embodiments, the engineered tissue substitute system may include the composition described herein and may be useful for the treatment of wounds in a subject requiring such treatment. A wound may be present in a subject may be derived from a variety of causes, including but not limited to injury, burns, surgical procedures, infection, pressure ulcers, diabetic ulcers, surgical and non-surgical trauma. The engineered tissue substitute system described herein is advantageous for such treatment in that it may be administered as a viscous liquid, allowing the composition to cover and fill the complex and irregular contours of the wound, following which is can become a continuous, solid gel. The compositions may be administered by injection, for instance using a syringe. In other embodiments, the compositions may be administered in a dry powder form and reconstituted in situ, allowing rapid formation of the cellular dermal scaffolds within minutes. The powder may be solubilized with a patient's whole blood, serum, or plasma in effort to create a growth factor enriched environment or simply mixed with distilled water. Once formed these scaffolds naturally assume an architecture that is similar to native dermis, and allow migration of cells, matrix proteins and other important factors into the scaffold architecture to facilitate improved healing.

When time is of the essence, the benefit of a patient ready skin substitute can be fully realized. The engineered tissue substitute system comprising a composition as described herein may be fabricated with or without cells at the bedside and be used to fill a wound bed and completely integrate with the wound surface. The stability of the lyophilized powder form of the composition is superior to existing hydrated materials such as hydrogels and cellular skin substitute, and the ability to reconstitute the powder into a scaffold that can mould to the wound site (with or without cells) confers greater utility over commercially available skin substitutes.

Composition Preparation Methods (A) 9 Step Method

1) Crosslinking of collagen and chondroitin-6-sulfate near neutral pH.

2) Addition of polyvinyl-alcohol based polymer hydrogel.

3) Addition of borate and Ascorbic acid.

4) Freezing of the foregoing combination of steps 1-3.

5) Freeze drying.

6) Grinding dried freeze dried product into a powder.

7) Resuspending powder in aqueous, biological or non-biological solvent.

8) Optionally adjusting the viscosity with a biologically inert agent, such as a shear-thinning agent, such as guar gum or shear thickening, such as agent dextran.

9) Optionally combining the resuspended powder in autologous, allogeneic or xenogeneic cells.

(B) Alternative Collagen Composition Preparation Method

Final Storage Conditions a liquid: 4° C. and minimize exposure to light.

As a powder: Air-tight container, 22° C. and minimize exposure to light.

Materials:
Tips: P1000, P200, P10
Scissors
TC tubes
1.7 mL microfuge tubes
ddH2O
10× Collagen Buffer
50% glutaraldehyde (−20° C.)
1N NaOH (Sterile Filtered)
20% Chondroitin Sulfate
Collagen (6 mg/ml or greater—Advanced Biomatrix)

20% Dextran
20% Glycine
5% and 10% PVA
0.2% w/w borate solution
10 mM Ascorbate
1×DMEM (complete media)
Reagents Preparation:
10× Collagen Buffer
10 ml 10×DMEM (pH 7.5)
10 ml 10×HEPES (pH 7.5)
9 ml 10×PBS (pH 7.0)
1 ml Antibiotic/Antifungal
20% Chondroitin Sulfate
1 g chondroitin Sulfate (shark cartilage—SIGMA™)
5 ml 1×PBS
Vortex repeatedly and warm at 37° C. to assist dissolution. Filter if possible using 0.4 μm filter.
20% Dextran
1 g dextran (SIGMA™)
5 ml 1×DMEM (w/o FBS and Antibiotic)
20% Glycine
4 g glycine
20 mL of 1×DMEM w/o FBS and Antibiotic
Adjust pH to 7.5 and store at room temperature.
10% PVA-99
5 g PVA-88% hydrolyzed LMW/5 g PVA-99% hydrolyzed HMW
100 mL of ddH2O
1. Heat water to 80° C. with overhead mixer.
2. Slowly add the HMW 99% until dissolved.
3. Slowly add the LMW 88% until dissolved.
15% Kollicoat™ IR
15 g of Kollicoat™ IR/100 ml of ddH2O
1. Heat water to 80° C. with overhead mixer.
2. Slowly add the Kollicoat™ IR and mix until dissolved.
Mix together 10% PVA with 15% Kollicoat™ in equal parts (50 ml/50 ml) and then add 2 mL of glycerol. Dilute to working solution (5%) using 10× collagen buffer.
25 mM Borate (0.2% w/w Borate)
1. Weigh 200 mg of sodium tetraborohydrate "borate"
2. Add borate to 10 ml of 1×DMEM (no supplements)
3. Mix well. pH should be between 8-9.
4. Dilute 1:10 in for working concentration of 6.25 mM (or 25 mM borate)
5. Store at 4° C. and make fresh if precipitate presents.
10 mM Ascorbic Acid in Distilled/Deionized Water (Make Fresh/Sterile Filter)

| Total Vol | Total Volume | 5.0000 |
| --- | --- | --- |
| Collagen 9.9 mg/ml | (total vol × 3) ÷ 9.9 | 1.5152 |
| 10× Buffer | total vol ÷ 10 | 0.5000 |
| 1N NaOH | col × 0.01 | 0.0152 |
| 20% GAG | ((col × 9) × 5) ÷ 200 | 0.3409 |
| 1.5% Glut | 0.0002 × total vol ÷ 0.015 | 0.0667 |
| 20% Glycine | 5 × glut | 0.3333 |
| 5% PVA | (total vol × 0.006) ÷ 0.05 | 0.6000 |
| 10 mM Ascorbate | (0.0001 × total vol) ÷ 0.01 | 0.0500 |
| 0.5 mM Borate | (total vol × 0.0005) ÷ 0.02 | 0.1250 |
| Volume Cells | total vol − (rxn vol) | 1.4538 |
| void volume (%) | 29% | |

Method
1. Prepare a clean (with ethanol 70%) 250 ml beaker with ice in the BSC.
2. Place 2-15 mL tubes in the ice.
3. Using a p1000 add collagen to one of the tubes. When finished eject the tip into the empty tube on ice.
4. Using a clean p1000 tip add collagen buffer to collagen.
5. Mix buffer and collagen together using the collagen tip stored on ice in the 15 mL tube. Before mixing eject remaining collagen, and then cut the tip of the tip to create a low viscous tip.
6. Using a p10 add 1N NaOH to the solution to neutralize the collagen to pH 6.8-7.5 (peachy colour). Add a maximum of only 15 ul at once. Mix well in between using the cut p1000 tip.
7. Once neutralized, add GAG (Chondroitin 6-sulfate) using a p1000 tip. Discard tip after use. Mix using the cut p1000 tip.
Lights Off (in Dark)
8. Turn the lights off. In a microfuge tube add 94 ul of dextran solution.
9. Add 6 ul of glutaraldehyde to the tube with dextran. Invert and finger vortex once. Quickly add the working solution of glutaraldehyde to the collagen mix. Mix well (2 min approximately) using the cut pipette tip. Avoid bubbles. pH is important. Ideal crosslinking pH is 7.5-8. (NB if too acidic the glutathione will not crosslink).
10. Incubate on ice in the dark for 22 min.
11. After 1 hour add glycine solution and mix well. This neutralizes the glutaraldehyde.
12. Incubate for minimum 1 hour on ice or O/N at 4° C. in the dark.
Lights on
13. Add Ascorbate to Collagen Gel and mix well.
14. Dilute PVA (10%) to working concentration of 5% using collagen buffer.
15. Add PVA working solution to Collagen Gel and mix well (approximately 1-2 min). Avoid creating bubbles.
16. Add Borate Buffer to Collagen Gel and mix well.
17. Store resulting Collagen Gel (now the complete IPN-hydrogel crosslinked collagen matrix) at 4° C. (Refer to storage conditions.)
Lyophilization
18. Estimate actual volume of reaction mixture by looking at the markings on the 15 mL tube. Weigh the tube. Record measurements (volume and weight).
19. Place the tube on its side in the −80° C. Freezer for 12 hours.
20. After 12 hours, turn on the lyophilizer (See manual).
21. Place tubes in the lyophilizer for 36 h/10 ml of liquid.
22. After lyophilization weigh the powder and calculate reconstitution volume (average 60-70 mg/mL).
(C) Alternative Composition
An alternative composition may have between 3-5 mg/ml of collagen; a 6:1 ratio of chondroitin sulfate (in 1×PBS): collagen; Glutaraldehyde (with later addition of glycine, where the glycine is added to neutralize the glutaraldehyde); 0.4%-0.6% weight PVA (pH 7.0) 10% HMW/MMW 50/50 99% hyd/88%; 0.01% (w/v)-0.0001% (w/v) Sodium borate decahydrate (pH 8); 100 μm Sodium ascorbate (pH 7.0); 3.5-5 μM Genepin (2° crosslinker); and 1-3 U Transglutaminase (all concentrations are for the final product).
Effect of Cross-Linker Concentration, PVA and Time on Fibril Formation:
In order to optimize the formulation of the gel with respect to changes in stock collagen concentration the effect of both glutaraldehyde concentration and crosslinking incubation time on the change in fibril formation rate was investigated. First, when a change in glutaraldehyde concentration was proportional to a change in stock collagen concentration (where 6 mg/ml was previously utilized; Hartwell et al., 2011) the crosslinking reaction would result in gel solidification on ice. As such, it was found that increasing the concentration of would actually decrease the gelation rate, rather than increase it as might be predicted (FIG. 2A; condition C1). Furthermore, higher concentrations of cross-linker resulted in a higher initial absorbance at 313 nm. This pattern continued within the reaction-volume matched samples, which contained less glutaraldehyde cross-linker (C2). Collagen alone, without cross-linker exhibited the lowest initial absorbance and highest final absorbance, together with the fastest fibril formation as shown in FIG. 2A. Again t½ max decreased, slightly, with the duration of incubation within the volume-matched reaction groups (FIG. 2A). It was apparent that a higher glutaraldehyde concentration in the reaction also corresponded to a reduction in t½ max that was proportional to incubation time. This reduction in gelation time would ultimately correspond to both a reduction in the formulation time and time for gel solidification as a working mixture. Interestingly, when the incubation time was adjusted for the stock concentration of collagen used in the reaction vessel (FIG. 2B) the reaction kinetics could be controlled. This result demonstrated that the optimal final concentration of cross-linker is 0.02% w/v and that crosslinking incubation time should be adjusted in proportion to the stock concentration (reaction vessel concentration) of collagen.

The effect of polyvinyl alcohol-hydrogel addition to the gel-mixtures demonstrated an increase in rate of fibril formation when the concentration of PVA is increased from 0 to 1.0% w/v, which corresponded to a significant reduction in activation energy (FIG. 3). As shown in TABLE 3, the addition of 1% w/v PVA resulted in more than 50% reduction in the required activation energy for fibril formation.

TABLE 3

Effect of polyvinyl alcohol-borate gels on activation energy of collagen fibrillation.

| [PVA] | Ea (J/mol) |         | $R^2$ | P value |
|-------|------------|---------|-------|---------|
| 0     | 2602.86    | ±424.88 | 0.93  | *       |
| 0.2   | 2524.42    | ±487.56 | 0.90  |         |
| 0.4   | 2025.82    | ±240.48 | 0.96  | **      |
| 0.6   | 1504.28    | ±280.20 | 0.91  | 0.00035*/0.00612** |
| 0.8   | 760.95     | ±237.50 | 0.78  | <0.0001*/** |
| 1     | 1276.45    | ±399.88 | 0.78  | 0.00024*/0.001** |

The slight increase in gelation rate was also associated with a decrease in overall gelation time. However, this change was not significant in the present assays. Toward the formulation of a scaffold that could cast within a wound bed, or in the working range of 30° C.-37° C. for cell delivery and transplantation, gel-mixtures containing different PVA-hydrogel concentrations were explored. The results demonstrated that the PVA-(borate) hydrogels could in fact alter the fibril formation kinetics of Type I bovine collagen, in order to permit gelation at 30° C. Where typical inverted test-tube tests may demonstrate gelation at these lower temperatures, evaluation of turbidity at 313 nm wavelengths remove the possibility of the PVA-hydrogel system to present artifact.

PVA-Hydrogel Addition Preserves Gelation and Mechanical Properties of Gel-Mixtures Following Lyophilization:

As an attempt to increase the stability of the gel-mixture (for transport and storage purposes), mixtures were lyophilized, ground into a powder and then reconstituted. Lyophilized mixtures were reconstituted with deionized and distilled water, without the need for pH neutralization. PVA-hydrogel systems that were created using a PVA-PEG co-polymer (Kollicoat™) were most easily reconstituted. Collagen scaffold variants that were not crosslinked and did not contain PVA exhibited significantly longer gelation times when compared with the matched non-lyophilized scaffold mixture (52.6 min±1.52 v. 36 mm±1.73) (FIGS. 4 & 5). The crosslinked-only (xcol) scaffolds were able to form fibrils, yet at a significantly longer gelation time than prior to lyophilization. Liquid mixtures of scaffold variants that contained PVA-hydrogels exhibited initial absorbances that were slightly higher than prior to lyophilization, yet formed fibrils within a statistically similar amount of time (FIGS. 4 & 5). The Kollicoat™ samples, most notably K99, were among the fastest to gel (15.7 min±1.16) and exhibited the smallest change turbidity (from t=0 to tmax absorbance) suggesting that that the PVA-PEG must have had a protective effect on the collagen structure in powder form, and again when reconstituted. As shown in FIGS. 4 & 5, PVA-hydrogel scaffolds exhibited a significant reduction in gelation time when compared with col, xcol, TW80™ and Tritonx100™ variants. The greatest reduction in gelation time was observed in scaffolds that contained the PVA-PEG hydrogels (2.02 fold). In comparison to previous studies that examined the effect of surfactants on collagen gelation kinetics (Fathima and Dhathathreyan, 2009; Li, 2009) Tween 20™, Tween 80™ and Triton-x100™ were combined within gel mixtures at their respective central micelle concentration's. (Note: The effect of Tween 20™ was comparable to Tritonx100™ and therefore was omitted for figure clarity). As shown in FIGS. 4 & 5, all surfactants increased the gelation rate (lowering $t_{1/2max}$) of both pre- and post-lyophilized samples, but to a significantly lesser extent than a majority of the PVA's.

PVA-PEG and PVA-Hydrogel Systems Exhibit a Surfactant Like Effect on Collagen Gel-Mixtures:

A primary role of surfactants is to improve the hydrophilicity of a hydrophobic surface. The addition of Tween 20™, Tween 80™ and Triton-x100™ to the collagen gel mixtures significantly reduced the aqueous contact angel of a water droplet sitting on top of a casted, thin-film of a gel mixture from 108° (Collagen:GAG) to 51, 75° for Triton X100 and Tween 80 respectively (FIG. 6). Additionally, there were differences in the contact angle depending upon the type of PVA that was used. Interestingly, when omitting borate (PVAnb) from the system the contact angle increased significantly from (52° to 72°). The crosslinked only gel-mixtures demonstrated the lowest contact angle suggesting the most hydrophilic surface formed by all gel mixtures (37°). PVA99, PVAnb and Tween 80™ were relatively similar at 75°, 76° and 75° respectively. Whereas Kollicoat™ 99 and 88 blends were the next most hydrophilic with contact angles at 58° and 53° respectively. As would be expected the more hydrophobic PVA's had a greater surfactant-like effect and therefore a greater reduction in contact angle compared to similar molecular weight PVA's.

Cell Viability and Cell Migration:

Cells cultured in gel-mixture variants were cultured for 24 hours within scaffolds prior to staining. All scaffold variants were found to be non-toxic in vitro (FIG. 7). Similar fibroblast populated collagen lattices were created to evaluate the migration. A punch biopsy was taken from the center of the scaffold and then filled with a matched acellular gel. There was no significant difference in cellular migration among all the scaffolds, with exception of the uncrosslinked, collagen:GAG scaffolds which exhibited the highest rate of cellular migration over a ten day period (FIG. 7B). On day 10, significantly more migrated cells were found in the k99 and xcol variants compared to PVA50/50 (FIG. 7B).

Fibroblast Morphology and Scaffold Architecture:

FIG. 8 depicts the morphology of fibroblasts cultured within five different scaffold variants. As found in previous studies, cells cultured within an uncrosslinked collagen scaffold exhibit extensive spreading of lamellapodia and filapodia extensions, of stress fiber formation (filamentous actin) with phalloidin-488 stain—micrographs not shown (Kim et al., 2014; Mattila and Lappalainen, 2008). Notable parallel fiber arrangement and reduced dendritic appearance, consistent with fewer filopodia, was observed fibroblasts cultured within a scaffold variant that contained a 50% wt Kollicoat™/50% wt PVA99 hydrogel (0.4% wt). Surfactant containing scaffolds exhibited a dendritic-like appearance with narrow filopodia-like extensions, and smaller cell bodies that are suggestive of cell stress and possible poor adhesion even though the cells remain viable (FIG. 7). Scanning electron microscope cross-sectional images (FIG. 8) recapitulated our findings in the previous work, whereby larger pore structures and thinner collagen fibers is evident in the non-crosslinked scaffold (col) compared to other crosslinked scaffold variants. Interestingly surfactant treatment with tween80™ (tw80) depict thicker collagen fibers, with a smaller pore and a more tortuous void-path through the scaffold.

Materials and Methods

Materials:

Type I fibrous-bovine collagen (Advanced Biomatrix™, USA), polyvinyl alcohol (PVA) 88% and 99% hydrolyzed (Alfa Aesar™, USA), Kollicoat IR™ (polyethylene-glycol (PEG)-PVA) (Sigma Aldrich™, Oakville, Canada), sodium tetraborate-decahydrate (borate) (Sigma Aldrich™, Oakville, Canada), glutaraldehyde (25% v/v, Sigma Aldrich™, Oakville, Canada), Dulbecco's Modified Essential Medium (10×, Life Technologies™, Canada), Chondroitin-6-sulfate (GAG) (Sigma Aldrich™, Oakville, Canada), Dextran™ (40,000 Da, Sigma Aldrich™, Oakville, Canada), Ascorbic acid (Sigma, Aldrich™, Oakville, Canada), Tween20 (Sigma Aldrich™, Oakville, Canada), Tween80™ (Sigma Aldrich, Oakville, Canada), Sodium dodecyl sulfate (Sigma Aldrich™, Oakville, Canada), (Live/Dead viability assay kit (Molecular Probes™, Invitrogen™, Canada), Phalloidin-488 Alexa Fluor™ (Invitrogen™, Canada).

Fabrication of Collagen-Polymer Hybrid Scaffolds:

Type I fibrous-bovine collagen in 1N HCl was combined with a collagen buffer (10×DMEM, 10×PBS, 10×HEPES and 1× Antibiotic, pH 7.5) and pH adjusted using 1N NaOH as depicted in FIG. 1. Once neutralized Chondroitin-6-sulfate was added to scaffolds (1:6, collagen:C6S). Non-crosslinked controls were combined with either remaining hydrogel reagents, or DMEM (1×). Crosslinked Gels were mixed thoroughly with a high molecular weight dextran (40,000 Da)-glutaraldehyde mix (0.02% v/v or as reported in TABLE 1) and allowed to incubate on ice in the dark. Incubation times varied as per the concentration and experimental object as outlined in TABLE 1. To optimize the cross-linker effects, gel-mixtures were exposed to glutaraldehyde concentrations that were either of proportion to a reaction volume (c1) or to the amount of collagen (c2) (FIG. 2A) or proportional to the incubation time (FIG. 2B). Different time periods were selected for each of the two treatment conditions such that exposure would be similar.

TABLE 1

Crosslinking conditions for scaffold variants depicted FIGURE 2.

| Scaffold | Stock Collagen | Glutaraldehyde | Incubation time |
|---|---|---|---|
| Col | 9.9 mg/ml | — | — |
| C1/45 | 9.9 mg/ml | 0.013% w/v | |
| C1/60 | 9.9 mg/ml | 0.013% w/v | |
| C1/70 | 9.9 mg/ml | 0.013% w/v | |
| C1/90 | 9.9 mg/ml | 0.013% w/v | |
| C2/15 | 9.9 mg/ml | 0.032% w/v | |
| C2/30 | 9.9 mg/ml | 0.032% w/v | |
| C2/60 | 9.9 mg/ml | 0.032% w/v | |
| FIG. 3.2.B. 60 min | 9.9 mg/ml | 0.02% w/v (reaction volume corrected to represent stock collagen of 6 mg/ml) | 60 min |
| FIG. 2B. 42 min | 9.9 mg/ml | 0.02% | 42 min |
| FIG. 2B. 21 min | 9.9 mg/ml | 0.02% | 21 min |

TABLE 2 describes the composition of variants used in all other investigations which followed the same crosslinking procedure as found in the variant in TABLE 3 "FIG. 2B 21 min". Following incubation polymer hybrid gels were combined with respective amounts of PVA or PVA-PEG copolymer and gelling agent (sodium tetraborohydrate decahydrate, 0.04-05% w/v) in a 1:4 ratio of borate molecule to hydroxyl functional group. All gel-mixes were brought to a final volume with 1×DMEM and ascorbic acid (100 uM). Gel-mixes were stored at 4° C. until casted or frozen at −80° C. for lyophilization. Select scaffolds were lyophilized (freeze-dried) for 36 hours, then ground into a powder using a mortar and pestle and reconstituted to their original concentration using distilled and deionized water.

TABLE 2

Composition of scaffold variants.

| Scaffold | Collagen (final) | Glutaraldehyde (final) | Additive |
|---|---|---|---|
| Collagen (Col) | 3 mg/ml | — | — |
| Crosslinked collagen (xCol) | 3 mg/ml | 0.02% w/v | — |
| (50/50) | 3 mg/ml | 0.02% w/v | 0.4% w/v of a 48% PVA (99% hydrolyzed)/48% PVA (88% hydrolyzed)/2% w/v glycerol and 0.05% wt borate |
| K99 | 3 mg/ml | 0.02% w/v | 0.4% w/v of a 48% PVA (99% hydrolyzed)/48% Kollicoat IR ®/2% w/v glycerol and 0.05% wt borate |
| K88 | 3 mg/ml | 0.02% w/v | 0.4% w/v of a 50% PVA (88% hydrolyzed)/48% Kollicoat IR ®/2% w/v glycerol and 0.05% wt borate |
| PVAnb | 3 mg/ml | 0.02% w/v | 0.4% w/v of a 48% PVA (99% hydrolyzed)/48% PVA (88% hydrolyzed)/2% w/v glycerol |
| TW80 | 3 mg/ml | 0.02% w/v | 0.012 mM Tween80 |
| TritonX100 | 3 mg/ml | 0.02% w/v | 0.022 mM TritonX100 |

Cross-Linker, Polyvinyl Alcohol and Copolymer Effects on Gelation Kinetics:

Gel-mixes were aliquoted (150 ul/well) into a 96 well plate on ice. Gelation kinetics were captured using a heated plate reader (Tecan™, USA) with a 313 nm uv/vis polarized filter set and Magellan Software™. The plate reader was first heated to the appropriate temperature (30, 32, 34, 37° C.) and measurements were captured at either 1 or 2-minute intervals. Three batches (triplicate) of gel variants were used for each analysis (n=3) unless otherwise reported. Turbidity is the best indicator of collagen fibrillogenesis, and more indicative of gelation when combined with translucent hydrogels such as PVA and PEG (Valli et al., 1986; Li, 2009; Panitch et al., 2011; Hartwell et al., 2011). The time to gelation is represented by the time at half the maximum absorbance at 313 nm. The lag time is the time from the start of gelation to the time at half the maximum. The slope of the curve dA/dt indicates the rate fibrillogenesis. Using the Arrhenius equation (1) the activation energy can calculated using first order kinetics of gel variants at different temperatures plotted as ln k vs. 1/T, where k is the rate constant and T is the temperature in Kelvin. The rate constant for a first order reaction can be derived from the gelation time ($t^{1/2}$) using equation (Terketaub, 1998).

$$\ln k = \ln A^{-Ea/T} \qquad (1)$$

$$k = \ln(2)/t_{1/2} \qquad (2)$$

Using similar principles the change in rate fibrillogenesis (dA/dt) with respect to the polymers can also be determined through the comparison of the slope of the curve in the linear region.

Mechanical Strength:

Gels were cast in 5-well rectangular chamber slides (400 ul each) and incubated for 24 hours at 37° C. Tensile testing was done using a KES-G1 Micro-Tensile Tester™ (Kato Tech™, Japan), with a 1 kg load cell. Prior to loading, gels were dried of excess liquid using KimWipes™ (Kimberly Clark™, USA) and weighed. Two pieces of KimWipe™ were then used to firmly secure the gel onto the specimen holder. Gels were then stretched until breaking at a deformation rate of 0.02 cm/s. Tensile strength was calculated by dividing breaking load (g) with sample width (mm) and area density (g.sq.m) of the polymerized gels. For statistical purposes, three batches of gel were evaluated.

Scaffold Architecture:

Collagen scaffolds (100 µl) were cast in 96 well plates for 24 hours followed by fixation in 4% Formalin solution for 24 hours at 4° C. After fixation the gels were dehydrated twice for 12 hours in 70% ethanol and then frozen at −80° C. prior to lyophilization. Lyophilized scaffolds were then weighed and evaluated on a Q1000 Differential Scanning Calorimeter™ (TA Instruments™, USA) at 5° C./min within a range of 20° C. to 100° C. SEM samples were first gold coated prior to loading inside the vacuum of a Hitachi S4700 SEM™ (Hitachi™, Japan).

Contact Angle:

Gel-mixtures were formulated as described and then cast into thin films on glass slides at 37° C. and then allowed to dry in a laminar flow hood for 24 hours. Using a contact angle tool (KSV Instruments™), contact angle of a water droplet on the surface of the thin film was calculated using Attention Theta Software V4.1™.

Cell Viability:

Viability was assessed using Live/Dead toxicity assay. Cells (primary or cell line) were cultured for in scaffolds for 24 hours. After 24 hours, scaffolds containing cells were washed 3 times with 1×PBS (pH 7.0) and a mixture of ethidium-homodimer and calcein-AM according to manufacturer's instructions. After 30 min scaffolds were washed 3 times with 1× PBS and visualized using a Zeiss Axiovert™ 200M fluorescent microscope and Axiovision™ software. Cell counts were obtained using Image J™ software (National Institutes of Health, USA).

Cell Adhesion and Migration:

Cell attachment and spreading was evaluated using phalloidin-Alexa-fluor 488™ for staining of actin in fibroblasts cultured within collagen scaffolds 24 and 48 hours after casting. Briefly, gels were created and combined with cells as per the assessment of cell viability. Evaluation of cellular migration consisted of creating 4 mm punch biopsies in the center of the gels and then filling the hole with de-cellularized gel. Images were captured over a 10-day period, and migrating cells were designated as those that crossed into the new gel from the margin of the old. Images were captured using a Zeiss Axiovert™ 200M fluorescent microscope and Axiovision™ software.

Statistics:

The number of repeats represents different batches of gels. Experimental results were evaluated using Analysis of Variance (ANOVA) with a post-hoc Tukey Test. Error calculations for linear regression represent the mean standard error of the fit for a given $R^2$ value of triplicate samples. Statistical significance was estimated with an alpha value of 0.05 (p<0.05). Measurements were reported as means±standard deviation.

EXAMPLES

The following examples are provided for illustrative purposes, and are not intended to be limiting, as such.

Example 1—Development of Engineered Tissue Substitute

A patient-ready skin substitute could be the answer to numerous unmet market needs in wound care. In order to facilitate the fabrication of patient-ready skin, with sustainable logistics, the skin substitute needs to form within the wound. Not only will this reduce product costs, but the matrix would also fits perfectly within the wound and fully integrates with the wound bed, improving rate of graft-take. As there are many methods to engineer an extracellular matrix the preferred route will require minimal modification from the physiological norm. Our rationale in the design of a scaffold that could satisfy these needs led to the creation of a bio-hybrid gel that contained both hydrogel and collagen. Early results demonstrated that a hydrogel comprising of PVA-borate could be added to a soluble, cross-linked collagen-GAG network to speed up fibril formation (and gelation) at 37° C. The rigidity of the collagen and polyvinyl alcohol improved the mechanical strength of the gelled scaffolds, and reduce the susceptibility to contracture. Furthermore, it was shown that the gelled scaffolds exhibit reduced cellular proliferation when compared with simple collage-GAG (uncrosslinked/crosslinked scaffolds). When used for transplantation of fibroblasts in vivo, the gel demonstrated its efficacy as a tissue substitute, as observed in both skin grafting in mice, rats and rabbits as well as in islet transplant in mice. Neovascularization occurs at a greater rate in wounds treated with the in-situ forming skin (with and without non-rejectable cells). Innervation into the tissue was also improved over a 30-day time course and cultured cord cells were able to grow and arrange into linear networks within the scaffold. Unique to this scaffold is that cells align in a polarized arrangement (linear) similar to that found in a tendon or cornea.

Example 2—Development of Improved Formulation, Including Dry Lyophilized Form

Previously we demonstrated that the combination of a PVA-borate hydrogel and a collagen-GAG scaffold resulted in a superior extracellular matrix when compared to a simple crosslinked collagen-GAG gel. The resulting composite gel exhibits a faster rate of gelation, reduced contracture and increased tensile strength. Biocompatibility was evaluated using a live/dead stain which demonstrated that fibroblasts, keratinocytes, epithelial cells and immortalized cells (HaCats) remain viable and proliferate at a reduced rate compared to both other scaffolds and culture plate surface. Since the original discovery we have refined the formulation to produce a gel that could be assembled and stored as one part. The upside with a single part gel that any simple syringe can be used to apply the gel, the downside is that overtime phase separation occurs. Secondly the uncasted gel system was insufficiently thixotropic. To overcome these issues two changes were made to the formulation. The first changes explored the concept of thickening the uncasted gel system by increasing the concentration of collagen, and by evaluating a range of PVA/Borate concentrations. As a result we have now identified a range of concentrations that are optimal, and prevented phase separation. Secondly, we discovered that the gel resin can be lyophilized and reconstituted. Typically, when crosslinked collagen and PVA is dried and broken down into a powder, it is not easily reconstituted. Our preliminary results demonstrated that the powder could be reconstituted using distilled water, whole blood, serum and plasma simply by vortexing at room temperature. The resulting resin can than be stored chilled or used immediately to form a gelled scaffold. Although we have provided evidence that: 1) our skin substitute is less contractual relative to non-cross-linked gel, 2) It is resistant to digestion by proteases normally found in the wound milieu such as collagenase, 3) It can be freeze/dried and re-constituted which makes it attractive for commercialization, 4) It has a long shelf life, its physical and biological properties have not been compared with some similar products available in the market.

Example 3—Use of Engineered Tissue Substitute for Treatment of Wounds

Chronic wounds comprise the largest segment in wound care. With over 250 million people affected by diabetes each year, the diabetic ulcer remains as one of the most common and difficult to treat out of all the wounds in this segment. The current mode of application is via injection, using a syringe. The syringe is first heated up to initiate gelation (fibril denaturation and hydrogen bonding). Albeit that the syringe system permits ease of application there may be a more efficient mode of delivery, for instance using a heated syringe or using a heat gun (37° C.) following application. After application, the wound is dressed. For instance, wound dressing may employ the use of silicone sheeting, spray on urethane, PLGA nanofibre, Meptiel™, Tegaderm™, or other conventional wound dressings. The engineered tissue substitute may be administered in a variety of forms, including but not limited to: 1) dry application, 2) hydrated with distilled water, 3) hydrated with whole blood, 4) hydrated with serum, and 5) hydrated with plasma. Moving toward a successful treatment strategy for the diabetic wound, and as a demonstration of the utility of the compositions described herein in wound care in patients requiring such care, including human patients, the engineered tissue substitute system of the described herein is demonstrated for treatment of wounds generated in diabetic mice. Previously we have found that wounds in non-obese diabetic mice exhibit delayed wound healing, similar to that in humans. An insert is placed on each wound to prevent contracture. The wounds are covered with a Tegaderm™ dressing and a second application of the skin substitute is applied 24 hours following surgery. Animals are sacrificed once wound closure is complete (10-15 days approximately). Diabetes is controlled using insulin injections on a daily basis to maintain blood glucose levels below 20 mM.

Example 4—Inclusion of Stably Transfected Cells Expressing IDO as an Immunomodulating Factor The adeno-associated vector is an approved vehicle for gene therapy which when transporting the gene for Indoleamine 2,3 dioxygenase can be used to make an immunomodulating cell. In our previous work, we have demonstrated that IDO expressing fibroblasts and keratinocytes can be used to create solid, bi-layer skin substitutes that confer resistance to rejection by macrophages and CD4+ and CD8+ T cells. With advancements in gene therapy and regulatory body familiarization to these advancement, it is expected that the benefit of an IDO expressing cell line could soon be realized clinically in the field of cell transplantation. Wounds may thus be treated and evaluated as described in Example 3. The addition of the IDO cells to the engineered tissue substitute system will further improve the healing outcome and rate of wound closure, as evidenced by our previous data.

Example 5—Application of Biohybrid Scaffold by Method of Spray Application

The versatility of the biohybrid scaffold in the sol form to remain a homogenous mixture prior to gelation provides an opportunity to use the system as either 1) a cell delivery vehicle and thin scaffold for the layer, by layer application of epithelial cells over a large surface area, such as a burn; and/or 2) to be used for the improvement of seeding cells in 3D bioprinting applications. Furthermore, skin cells remain viable after a thin layer scaffold was formed using spray application of the reconstituted biohybrid scaffold comprising a composition described herein (FIG. 10).

Example 6—Application of the Biohybrid on Full Thickness Rabbit Ear Wounds with and without Cell Transplant Improves Hypertrophic Scarring and Healing Outcome Biohybrid scaffolds, both without cells (acellular) and with IDO expressing cells (described in Example 4) were applied to full thickness rabbit ear wounds (6 mm), which typically undergo hypertrophic scarring even when treated. On post surgical day 20 wounds treated with reconstituted biohybrid scaffold exhibited complete closure whereas untreated wounds and those treated with non-IDO xenogenic transplants did not. By Day 35 all wounds had completely healed. Non-IDO xenotransplants and untreated controls exhibited significant hypertrophic scarring (high cellularity, scarring elevation index) and immune cell (CD3+) infiltration. The acellular biohybrid scaffold and IDO-expressing cell scaffolds did not exhibit any signs of scarring. The biohybrid scaffolds were able to permit the successful transplant of IDO expressing cells, which remained viable for the study duration. Furthermore, biohybrid scaffolds permitted neovascularization and neoinnervation.

Example 7—Testing of K99 Reconstituted Scaffolds

Scaffold fabrication is core facet of tissue engineering. Modalities moving toward cell transplantation have prompted the demand for soft-materials that can conform to surrounding tissues, and exhibit tissue specific mechanical properties (strength, viscosity, elasticity, etc.) and physical characteristics (pore size, surface chemistry-, gel transition temperature) (Turner R. et al. Transplantation (2010); Al-Abboodi A. et al. Advanced healthcare materials (2014); Balakrishnan B. et al. Biomaterials (2005); Meng X. et al. Journal of biomedical materials research Part A (2013); Prestwich G D. Organogenesis (2008). Synthetic biocompatible polymers or modified biomaterials are often chosen for the creation of injectable scaffolds and hydrogels. Although type I collagen can also be used as an injectable material, it's gelation temperature (and time) retard its utility as an in situ forming scaffold. To circumvent this issue, it can be chemically modified through crosslinking in order to create a more viscous material that would also avoid rapid degradation because of the chemical crosslinks. Excellagen™ and Integra Flowable™ are two currently marketed injectable products for use as a dermal filler and wound healing modality respectively. Both Excellagen™ and Integra Flowable™ are new to the market, yet as soft materials are unable to form intact solid scaffolds (gels) in situ. Furthermore, most collagen scaffold preparations for tissue engineering research and clinical uses, first requires neutralization of a collagen solution prior to use. The utility of a reconstitutable collagen scaffold, as opposed to a gel-slurry, is that aside from forming in situ it would also have similar mechanical properties to preformed solid scaffolds, such as holding sutures or serving as an interface between an implant and tissue. Clinical utility of K99 reconstituted scaffolds as described herein were tested following reconstitution with distilled and deionized water, serum and whole blood. Reconstituted K99 scaffold was tested for viscosity within a 16G BD™ IV catheter and for suture holding ability in a gelled, reconstituted K99 scaffold (data not shown). It was found that the reconstituted polymer scaffolds described herein showed beneficial mechanical and physical properties as compared to available alternatives. For example, reconstituted K99 scaffold as described herein showed suitable strength and elasticity to hold multiple sutures.

REFERENCES

Al-Abboodi A. et al. "Injectable 3D Hydrogel Scaffold with Tailorable Porosity Post-Implantation" Advanced healthcare materials (2014) 3(5):725-36.
Alexy P. et al. "Polymeric water-soluble biodegradable material and method for its preparation" Published PCT Patent Application WO 2000061660 (PCT/SK2000/000005).
Amarpreet S S. "In situ polymerizable hydrogels" U.S. Pat. No. 6,818,018.
Balakrishnan B. et al. "Evaluation of an in situ forming hydrogel wound dressing based on oxidized alginate and gelatin" Biomaterials (2005) 26(32):6335-42.
Fathima N N, Dhathathreyan A. "Effect of surfactants on the thermal, conformational and rheological properties of collagen" Int J Biol Macromol (.2009) 45(3):274-8.
Franzblau C. et al. "Hydrogels capable of supporting cell growth" U.S. Pat. No. 4,565,784.
Gunther S. et al. "Hydrogel foams, and a process for their preparation" U.S. Pat. No. 5,147,344.
Hartwell R, Leung V, Chavez-Munoz C, Nabai L, Yang H, Ko F, et al. "A novel hydrogel-collagen composite improves functionality of an injectable extracellular matrix" Acta Biomater. (2011) 7(8):3060-9.
Hirofumi Y. et al. "Glycosaminoglycan/collagen complexes and use thereof" U.S. Pat. No. 7,226,611.
Kim M H, Sawada Y, Taya M, Kino-Oka M. "Influence of surface topography on the human epithelial cell response to micropatterned substrates with convex and concave architectures. Journal of biological engineering" (2014) 8:13.
Lamberti F V. et al. "Cross-linked bioactive hydrogel matrices" U.S. Pat. No. 7,799,767.
Li Y. "The Mechanism of Collagen self-assembly: hydrophobic and electrostatic interactions" [Dissertation]. Florida: University of Florida; 2009.
Mattila P K, Lappalainen P. "Filopodia: molecular architecture and cellular functions" Nature reviews Molecular cell biology. (2008) 9(6):446-54.
Meng X. et al. "Novel injectable biomimetic hydrogels with carbon nanofibers and self assembled rosette nanotubes for myocardial applications" Journal of biomedical materials research Part A (2013) 101(4): 1095-102.
Panitch J E P, A., Park K., Stuart K., Higbee S., inventor; Purdue Research Foundation, assignee. "Collagen-binding synthetic peptidoglycans, preparation, and methods of use" USA patent application US20110020298 A1. 2011.
Parenteau-Bareil, Rémi et al. "Collagen-Based Biomaterials for Tissue Engineering Applications" Materials (2010) 3:1863-1887).
Prestwich G D. "Engineering a clinically-useful matrix for cell therapy" Organogenesis (2008) 4(1):42-7.
Masao N. "Process for preparing a hydrogel" U.S. Pat. No. 4,664,857.
Nemeth G G B M, Martin G R. "Growth factors and other aspects of wound healing clinical implications" (1988) 1-17.
Renn D W. "Solid borate-diol interaction products for use in wounds" Published PCT Patent Application WO 1999053968 (PCT/GB1999/001033).
Sarti, B. and Scandola M. "Viscoelastic and thermal properties of collagen/poly(vinyl alcohol) blends" Biomaterials (1995) 16(10):785-92.
Sehl L C. et al. "Methods for tissue repair using adhesive materials" U.S. Pat. No. 6,833,408.
Suuronen, E J. et al. "Functional innervation in tissue engineered models for in vitro study and testing purposes" Toxicological Sciences (2004) 82(2):525-533.
Tacey X V. et al. "Medical uses of in situ formed gels" U.S. Pat. No. 6,136,334.
Terketaub R A G M. "The molecular and Cellular biology of wound repair" Springer Editors: Clark, Richard (Ed.) 1988.
Turner R. et al. Transplantation "The future of cell transplant therapies: a need for tissue grafting" (2010) 90(8):807-10.
Valli M, Leonardi L, Strocchi R, Tenni R, Guizzardi S, Ruggeri A, et al. "In vitro fibril formation of type I collagen from different sources: biochemical and morphological aspects" Connect Tissue Res. (1986) 15(4): 235-44.

What is claimed is:
1. A lyophilized powder composition, the composition comprising:
(a) collagen, wherein the collagen is at a concentration of between 3-10 mg/ml;
(b) glycosaminoglycan, wherein the ratio of the glycosaminoglycan to collagen is a weight ratio from about 4:1 to about 8:1;
(c) a biocompatible small molecule cross-linker of collagen and glycosaminoglycan;

(d) a hydrogel, wherein the hydrogel is 0.01%-1.0% w/vol of the final composition; and
(e) a biocompatible, small-molecule, hydrogel cross-linker.

2. The composition of claim 1, wherein the biocompatible small molecule cross-linker of collagen and glycosaminoglycan is selected from one or more of the following: glutaraldehyde, 1-ethyl-3-(3-dimethylaminopropyl) carbodiimide (EDAC), EDC (1-Ethyl-3-(3-dimethylaminopropyl)-carbodiimide):NHS (N-hydroxysuccinimide), EDC (1-Ethyl-3-(3-dimethylaminopropyl)-carbodiimide):sulfo-NHS (N-hydroxysulfoxuccinimide), hexamethylene diisocyanate and Genipin.

3. The composition of claim 1, wherein the hydrogel is formed from hydrogel polymers, and wherein the hydrogel polymers are selected from one or more of: polyvinyl alcohol (PVA); polyvinyl acetate (PVacetate); thiolated polyvinyl alcohol; polyvinyl alcohol block polymers containing polyethylene glycol (PVA-PEG); polyvinylpyrrolidone (PVP); and a copolymer thereof of any two or more of the preceding polymers.

4. The composition of claim 1, wherein the hydrogel is 0.01-0.5% w/vol of the final composition.

5. The composition of claim 1, wherein the composition further comprises a solvent.

6. The composition of claim 5, wherein the solvent is cell media, water, or a physiological fluid.

7. The composition of claim 6, wherein the physiological fluid is blood, serum or plasma.

8. The composition of claim 1, wherein fibrillogenesis begins within 13-16 minutes of solvent addition.

9. The composition of claim 1, wherein gelation of the powder occurs:
between 25°-40° C.;
between 25°-37° C.;
between 30°-37° C.; or
at 37° C.

10. A wound treatment method, the method comprising reconstituting the powdered composition of claim 1 in a solvent and administration of the reconstituted composition to a patient in need thereof.

11. A method of preparing a composition of claim 1, the method comprising:
(a) mixing collagen with glycosaminoglycan, wherein the ratio of the glycosaminoglycan to collagen is a weight ratio from about 4:1 to about 8:1;
(b) cross-linking of collagen and glycosaminoglycan;
(c) adding a hydrogel to the cross-linked collagen and glycosaminoglycan, wherein the hydrogel is 0.3%-1.0% w/vol of the final composition; and
(d) cross-linking the hydrogel.

12. The method of claim 11, wherein the cross-linking of collagen and glycosaminoglycan is by dehydrothermal treatment (DHT), ultraviolet irradiation (UV) or enzymatic crosslinking.

13. The method of claim 11, wherein the cross-linking of collagen and glycosaminoglycan is by small molecule cross-linker of collagen and glycosaminoglycan.

14. The method of claim 13, wherein the cross-linker of collagen and glycosaminoglycan is selected from one or more of the following: glutaraldehyde, 1-ethyl-3-(3-dimethylaminopropyl) carbodiimide (EDAC), EDC (1-Ethyl-3-(3-dimethylaminopropyl)-carbodiimide):NHS (N-hydroxysuccinimide), EDC (1-Ethyl-3-(3-dimethylaminopropyl)-carbodiimide):sulfo-NHS (N-hydroxysulfoxuccinimide), hexamethylene diisocyanate and Genipin.

15. The method of claim 14, wherein the method further comprises adding dextran.

16. The method of claim 11, wherein the hydrogel comprises one or more of: polyvinyl alcohol (PVA); polyvinyl acetate (PVacetate); thiolated polyvinyl alcohol; polyvinyl alcohol block polymers containing polyethylene glycol (PVA-PEG); polyvinylpyrrolidone (PVP); and a copolymer thereof of any two or more of the preceding polymers.

17. The method of claim 16, wherein the hydrogel is a PVA hydrogel.

18. The method of claim 17, wherein the PVA hydrogel is 0.4-0.6% w/vol of the final composition.

19. The method of claim 17, wherein the cross-linker of the hydrogel is:
borate; or
sodium borate decahydrate.

20. The method of claim 11, wherein the cross-linker is:
0.01%-0.0001% w/vol of the final composition; or
0.01-0.1% w/vol of the final composition.

21. The method of claim 11, wherein the method further comprises lyophilizing of the composition.

22. The method of claim 21, wherein the method further comprises powdering the lyophilized composition.

23. The method of claim 22, wherein the method further comprises reconstituting the powder in a solvent.

24. The method of claim 23, wherein the solvent is a physiological fluid or water.

25. The method of claim 24, wherein the physiological fluid is blood, serum or plasma.

* * * * *